US012303423B2

United States Patent
Hoggarth et al.

(10) Patent No.: US 12,303,423 B2
(45) Date of Patent: May 20, 2025

(54) OSTOMY APPLIANCE

(71) Applicant: CONVATEC LIMITED, Deeside (GB)

(72) Inventors: Marcus Hoggarth, London (GB); Oliver Poyntz, London (GB); Kimahni Emsley, London (GB); Daljinder Sanghera, London (GB)

(73) Assignee: CONVATEC LIMITED, Flintshire (GB)

( * ) Notice: Subject to any disclaimer, the term of this patent is extended or adjusted under 35 U.S.C. 154(b) by 977 days.

(21) Appl. No.: 17/061,804

(22) Filed: Oct. 2, 2020

(65) Prior Publication Data

US 2021/0100679 A1 Apr. 8, 2021

Related U.S. Application Data

(63) Continuation of application No. PCT/GB2020/052415, filed on Oct. 2, 2020.
(Continued)

(30) Foreign Application Priority Data

Oct. 4, 2019 (GB) ...................................... 1914346
Oct. 4, 2019 (GB) ...................................... 1914351
(Continued)

(51) Int. Cl.
*A61F 5/44* (2006.01)
*A61F 5/448* (2006.01)

(52) U.S. Cl.
CPC ............ *A61F 5/4407* (2013.01); *A61F 5/448* (2013.01)

(58) Field of Classification Search
CPC ..................................................... A61F 5/445
See application file for complete search history.

(56) References Cited

U.S. PATENT DOCUMENTS

| 5,250,042 A | 10/1993 | Torgalkar et al. |
| 5,690,623 A | 11/1997 | Lenz et al. |
| (Continued) | | |

FOREIGN PATENT DOCUMENTS

| CN | 106535836 A | 3/2017 |
| DE | 19752598 C1 | 8/1999 |
| GB | 1570181 A | 6/1980 |

OTHER PUBLICATIONS

International Search Report; European Patent Office; International Application No. PCT/GB2020/052415; Dec. 22, 2020; 5 pages.
(Continued)

*Primary Examiner* — Andrew J Mensh
*Assistant Examiner* — Meagan Ngo
(74) *Attorney, Agent, or Firm* — Taft Stettinius & Hollister LLP; Ryan O. White; Derek B. Lavender

(57) ABSTRACT

An ostomy appliance that has inner and outer walls of flexible sheet material joined together to define a cavity for containing a stomal output, the inner wall having an inlet for receiving the stomal output into the cavity and a retractable drain being slidably movable between an extended configuration for draining the stomal output from the cavity and a retracted configuration for storage of the retractable drain. The retractable drain comprises a closure portion which may be turned up to close an outlet opening of the retractable drain and a first fastener configured to fasten the closure portion in place once turned up.

14 Claims, 14 Drawing Sheets

Related U.S. Application Data

(60) Provisional application No. 62/911,144, filed on Oct. 4, 2019.

(30) Foreign Application Priority Data

| Oct. 4, 2019 | (GB) | .................................... | 1914352 |
| Oct. 4, 2019 | (GB) | .................................... | 1914356 |
| Oct. 4, 2019 | (GB) | .................................... | 1914357 |
| Oct. 4, 2019 | (GB) | .................................... | 1914358 |
| Oct. 4, 2019 | (GB) | .................................... | 1914376 |

(56) References Cited

U.S. PATENT DOCUMENTS

| 8,821,463 | B2 | 9/2014 | Grum-Schwensen | |
| 2003/0014023 | A1 | 1/2003 | Kanbara | |
| 2005/0159717 | A1* | 7/2005 | Holtermann | A61F 5/4407 604/332 |
| 2008/0033379 | A1* | 2/2008 | Pedersen | A61F 5/4407 604/335 |
| 2008/0300556 | A1 | 12/2008 | Fenton | |
| 2009/0082743 | A1* | 3/2009 | Buglino | A61F 5/4405 604/335 |
| 2011/0028924 | A1* | 2/2011 | Murray | A61F 5/4407 604/332 |
| 2011/0190718 | A1 | 8/2011 | Wheaton et al. | |
| 2012/0022477 | A1* | 1/2012 | Grum-Schwensen | A61F 5/443 604/332 |
| 2012/0283678 | A1 | 11/2012 | Nguyen-DeMary et al. | |
| 2013/0072885 | A1 | 3/2013 | Luther et al. | |
| 2013/0253455 | A1 | 9/2013 | Masters et al. | |
| 2013/0253456 | A1* | 9/2013 | Friske | A61F 5/4407 604/332 |
| 2014/0039430 | A1 | 2/2014 | Richmann et al. | |
| 2015/0320585 | A1 | 11/2015 | Fattman et al. | |
| 2016/0058604 | A1 | 3/2016 | Wiltshire et al. | |
| 2017/0209297 | A1* | 7/2017 | Lysgaard | A61F 5/4404 |
| 2019/0029868 | A1 | 1/2019 | Grum-Schwensen et al. | |
| 2021/0369494 | A1 | 12/2021 | Holden et al. | |

OTHER PUBLICATIONS

Written Opinion of the International Searching Authority; European Patent Office; International Application No. PCT/GB2020/052415; Dec. 22, 2020; 9 pages.

International Search Report; European Patent Office; International Application No. PCT/GB2020/052414; Dec. 8, 2020; 3 pages.

Written Opinion of the International Searching Authority; European Patent Office; International Application No. PCT/GB2020/052414; Dec. 8, 2020; 6 pages.

International Search Report; European Patent Office; International Application No. PCT/GB2020/052413; Dec. 10, 2020; 3 pages.

Written Opinion of the International Searching Authority; European Patent Office; International Application No. PCT/GB2020/052413; Dec. 10, 2020; 5 pages.

International Search Report; European Patent Office; International Application No. PCT/GB2020/052416; Jan. 19, 2021; 5 pages.

Written Opinion of the International Searching Authority; European Patent Office; International Application No. PCT/GB2020/052416; Jan. 19, 2021; 9 pages.

* cited by examiner

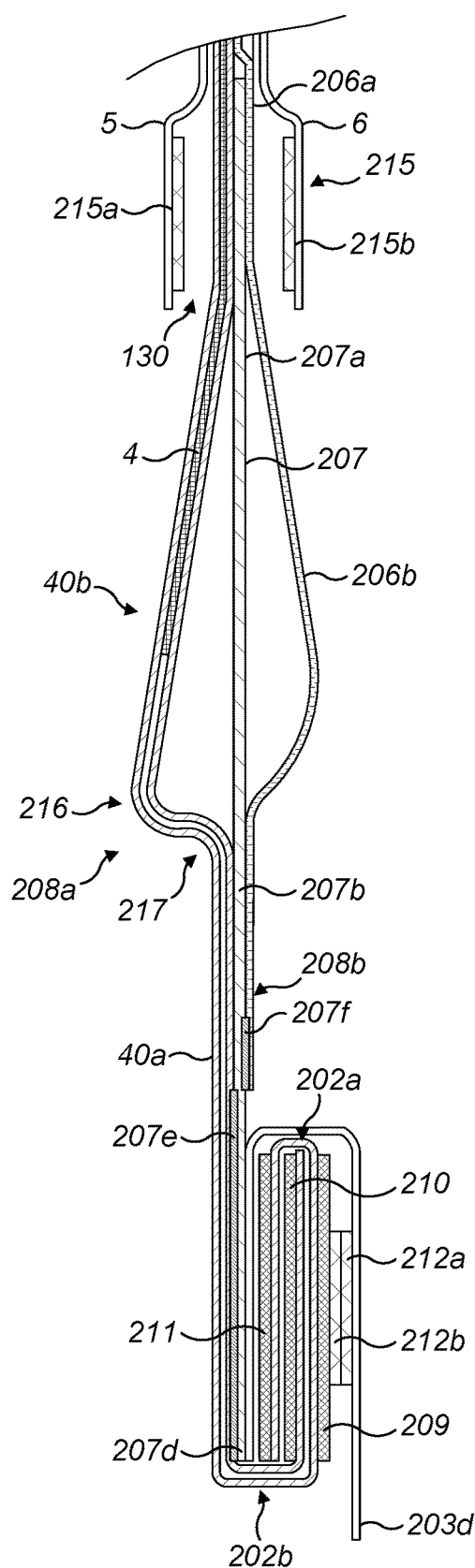
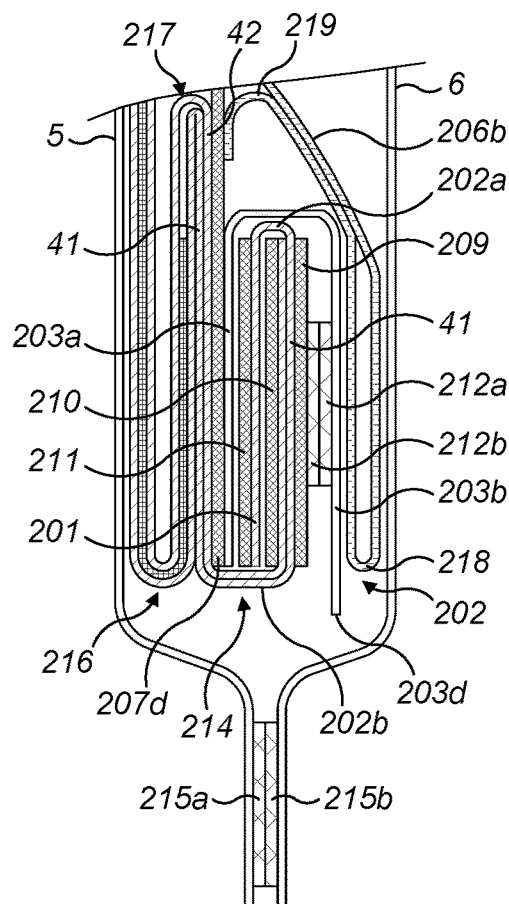
FIG. 9b
FIG. 9c

OSTOMY APPLIANCE

This application is a continuation of International Application No. PCT/GB2020/052415 filed Oct. 2, 2020 and claims the priority of foreign application Nos. GB1914357.7, GB1914352.8, GB1914346.0, GB1914356.9, GB1914376.7, GB1914358.5, GB1914351.0, and U.S. Provisional Application No. 62/911,144, all filed Oct. 4, 2019. The disclosures of which are hereby incorporated herein in their entirety.

TECHNICAL FIELD

The present disclosure relates to an ostomy appliance for managing effluent from a stoma.

BACKGROUND OF THE DISCLOSURE

There are many forms of ostomy appliance which try to provide an easily drainable appliance which can be securely sealed when to drain is not in use.

US2005159717 discloses a bag for collecting body fluids, such as excrement, for a person having undergone an ostomy. The bag comprises a receptacle pouch terminated by a neck, a discharge channel linked to said neck and having a waste opening, an opening/closing device to shift the discharge channel from a folded closed state to an unfolded opened state and comprising first and second opening/closing means arranged transversely relative to the discharge channel. A film of the receptacle pouch is provided externally with a rigidifying member proximate the neck and the second opening/closing means of the discharge channel is arranged, at least in folded closed state, in a slot located between the rigidifying member and said film of the receptacle pouch.

WO2017136304 discloses a drainable ostomy pouch including a collection pouch having a collection cavity, a retractable outlet movable between a first position retracted substantially into the collection cavity and a second position extending outwardly from the collection cavity, a discharge opening formed at a distal end of the retractable outlet and a closure configured to selectively allow or prevent discharge of a waste material from the collection cavity or the retractable outlet.

US2011028924 discloses a drainable ostomy pouch including a collection portion and a drain chute portion extending from the collection portion and having a discharge opening for permitting emptying of contents from the pouch. The drain chute is foldable between an open condition in which the drain chute portion is extended from the collection portion, and a closed condition in which the drain chute portion is folded towards the collection portion. At least one flap retains the folded drain chute portion.

There remains a need for ostomy appliances with enhanced usability for ostomates, particularly in the area of ease of use and improved sealing of the drain.

SUMMARY OF THE DISCLOSURE

In this specification, the term "stomal output" refers to any gases or fluids or solids produced by an ostomate that may be secreted from the stoma or that exit the stoma.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, teh term "ostomate" refers to a subject that may have use of the ostomy appliance disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

Beneficially, the ostomy appliances of the present disclosure may permit an ostomate to increase the period of use of each ostomy appliance compared to prior art appliances. This may be achieved, for example, by providing an increased cavity volume for the ostomy appliance while maintaining ostomate discretion and comfort. Additionally or alternatively, this may also be achieved by providing means for draining the cavity of stomal output reliably and hygienically so as to increase an ostomate's confidence in reusing the ostomy appliance compared to some prior art appliances. Since the ostomate may be inclined to use each ostomy appliance of the present disclosure for longer, the total number of ostomy appliances used by the ostomate in a given time period may be reduced. This may produce an environmental benefit in reducing the amount of environmental waste produced.

In this specification locations and orientations of features may be described with reference to the ostomy appliance being "in use", "orientated as it would be in use" or similar. Such terms refer to the intended orientation of the ostomy appliance when it is adhered to a body of an ostomate with the ostomate in a standing position, irrespective of whether the ostomy appliance is currently performing such a use or the actual position of the ostomate. The terms "upper" and "lower" and related terms refer to the relative position of a part or portion of the ostomy appliance when orientated as it would be in use. For example, a part such as an apex of the ostomy appliance may be referred to as an "upper" apex in use of the ostomy appliance. In such an example, said apex will be intended to be the uppermost apex (in the vertical direction) of the ostomy appliance when attached to the body of a standing ostomate. However the reader skilled in the art will appreciate that before attachment to the ostomate said apex may not always be the uppermost apex and in addition when attached the apex may not always be the uppermost apex if the ostomate adopts a non-standing position, for example lying down.

In this specification the terms "inner" and "outer" refer to the relative position of a part or portion of the ostomy appliance with reference to the body of an ostomate when the ostomy appliance is attached to the body. "Inner" refers to a position relatively closer to the body of the ostomate than a comparative position that is "outer". "Outer" refers to a position relatively further away from the body of the ostomate than a comparative position that is "inner".

In this specification the term "peripheral region" refers to a portion situated on or towards an edge of the item being referred to.

In this specification, the term "length" of a drain, refers to a dimension from an inlet of the drain to an outlet of the drain, along an elongate axis of the drain. The "length" dimension is measured along or parallel to the elongate axis. The term "depth" refers to a dimension from an outer portion to an inner portion of a component. The term "width" of the drain, channel or other component refers to a dimension across the drain, perpendicular to the length and depth.

The term "turned up" used herein may include folding or rolling of the components.

The present disclosure provides an ostomy appliance comprising:
  inner and outer walls of flexible sheet material joined together to define a cavity for containing a stomal output, the inner wall comprising an inlet for receiving the stomal output into the cavity; and
  a retractable drain being slidably movable between an extended configuration for draining the stomal output from the cavity and a retracted configuration for storage of the retractable drain;
  wherein the retractable drain comprises a closure portion which may be turned up to close an outlet opening of the retractable drain and a first fastener configured to fasten the closure portion in place once turned up.

The closure portion is preferably operable to be turned up and fastened while the retractable drain is in the extended configuration.

The retractable drain is preferably configured such that after fastening of the closure portion in the extended configuration, the retractable drain is slidably moveable into the retracted configuration.

Additionally or alternatively, in some embodiments the closure portion may be configured to be turned up by forming at least one fold across the retractable drain to inhibit passage of stomal output through the outlet end, wherein the closure portion is preferably configured to be folded into a plurality of folds across the retractable drain to inhibit passage of stomal output through the outlet opening.

Additionally or alternatively, in some embodiments at least a part of the first fastener may be arranged on an intermediate portion of the retractable drain such that the first fastener is adjacent to or overlapping the closure portion.

Additionally or alternatively, in some embodiments the first fastener may comprise:
  a first flange attached to the intermediate portion of the retractable drain adjacent to the closure portion; and
  a second flange comprising a first fastening element for attachment to the closure portion;
  wherein the closure portion preferably further comprises a second fastening element for attachment to the first fastening element.

Additionally or alternatively, in some embodiments the first fastener may be arranged across the width of the retractable drain.

Additionally or alternatively, in some embodiments the second flange may be configured to extend over the closure portion when fastened.

Additionally or alternatively, in some embodiments the ostomy appliance may further comprise a push element for pushing the retractable drain into the retracted configuration, the push element preferably comprising a strip of material having higher rigidity than the flexible sheet material of the inner wall and/or the outer wall.

Additionally or alternatively, in some embodiments the first fastener may be configured to be operable independently of the push element, and preferably wherein the push element and the first fastener are formed as separate components.

Additionally or alternatively, in some embodiments the retractable drain may further comprise a first pursing strip and a second pursing strip arranged on the closure portion of the retractable drain;
  wherein the or each pursing strip may comprise a strip of flexible material having higher rigidity that the material forming the retractable drain, the strip being arranged across a width of the retractable drain;
  wherein the first pursing strip may be arranged on an outer side of the retractable drain, and the second pursing strip arranged on an inner side of the retractable drain, the first pursing strip and the second pursing strip being positioned at the same distance along the retractable drain such that they are arranged opposite each other.

Additionally or alternatively, in some embodiments the ostomy appliance may further comprise a lip pursing strip arranged adjacent to the outlet opening of the retractable drain.

Additionally or alternatively, in some embodiments a plurality of pursing strips may be arranged adjacent to each other and spaced apart to define folding points of the retractable drain between the pursing strips such that the retractable drain is foldable in increments defined by a length of the pursing strips.

Additionally or alternatively, in some embodiments each of the pursing strips may extend the same distance along a length of the retractable drain.

Additionally or alternatively, in some embodiments the retractable drain may extend from a lower part such as a lower apex of the cavity.

Additionally or alternatively, in some embodiments the retractable drain may comprise one or more portions of flexible sheet material.

Additionally or alternatively, in some embodiments the retractable drain may comprise:
  an inner drain portion extending from a main body portion of the inner wall; and
  an outer drain portion extending from a main body portion of the outer wall;
  wherein the inner and outer drain portions are sealed at their lateral edges to define a drain passage between the inner and outer drain portions.

Additionally or alternatively, in some embodiments the inner drain portion may be integrally formed with the main body portion of the inner wall and/or the outer drain portion may be integrally formed with the main body portion of the outer wall.

Additionally or alternatively, in some embodiments one of the inner drain portion and the outer drain portion may be longer than the other of the inner drain portion and the outer drain portion, thereby defining a lip at the outlet opening of the retractable drain; and preferably wherein a pursing strip is arranged on the lip.

Additionally or alternatively, in some embodiments in the retracted configuration drainage of the stomal output from the cavity into the retractable drain and along the retractable drain may be inhibited by folds formed across the retractable drain during the sliding retraction; and/or wherein in the retracted configuration substantially all of the retractable drain may overlie a main body portion of the outer and/or inner wall.

Additionally or alternatively, in some embodiments in the retracted configuration the retractable drain may be received in a channel arranged on an outer face of the inner wall or an outer face of the outer wall; and preferably
wherein the channel is defined by a guide panel attached to a main body portion of the inner wall or a main body portion of the outer wall.

Additionally or alternatively, in some embodiments the ostomy appliance further comprises an inner comfort layer arranged over at least a part of the inner wall and an outer comfort layer arranged over at least a part of the outer wall;
wherein the inner comfort layer and/or the outer comfort layer may define an opening through which the retractable drain may be slidably moveable between the extended and retracted configurations; and
wherein a closure for closing the opening may be arranged at or near to a lower end of the channel such that the closure may restrict sliding of the retractable drain from the retracted configuration.

The present disclosure also provides a method of storing a retractable drain of an ostomy appliance comprising the steps of:
turning up a closure portion arranged adjacent to an outlet opening of the retractable drain to close the outlet opening;
fastening the closure portion in place using a first fastener arranged on an intermediate portion of the retractable drain; and
sliding the retractable drain into a retracted configuration.

The present disclosure also provides a method of draining an ostomy appliance comprising the steps of:
sliding a retractable drain from a retracted configuration to an extended configuration;
unfastening a first fastener arranged on an intermediate portion of the retractable drain; and
opening out a closure portion of the retractable drain to create an open drain passage from a cavity of the ostomy appliance to an outlet opening of the retractable drain.

Additionally or alternatively, the ostomy appliance of these methods may be an ostomy appliance as previously described.

The present disclosure also provides an ostomy appliance comprising:
inner and outer walls of flexible sheet material joined together to define a cavity for containing a stomal output, the inner wall comprising an inlet for receiving the stomal output into the cavity;
a retractable drain being slidably movable between an extended configuration for draining the stomal output from the cavity and a retracted configuration for storage of the drain; and
a guide panel arranged on the inner wall or the outer wall, thereby defining a channel for receiving the drain.
The channel is preferably configured such that the drain can be slidably received in the channel.

Additionally or alternatively, in some embodiments the guide panel may be attached to an outer face of a main body portion the inner wall or an outer face of a main body portion the outer wall such that the channel is formed outside the cavity.

Additionally or alternatively, in some embodiments the guide panel may be attached by welding or by adhesives.

Additionally or alternatively, in some embodiments an upper portion of the guide panel may be attached to the inner wall or the outer wall along a pair of lateral edges of the upper portion, thereby forming a pair of channel edges.

Additionally or alternatively, in some embodiments the channel edges may be generally parallel with each other along a majority of their length, and preferably wherein the channel edges are generally parallel with an elongate axis of the drain.

Additionally or alternatively, in some embodiments the channel edges may diverge at a lower end of the channel such that the channel comprises a mouth having an increased width compared to an upper portion of the channel.

Additionally or alternatively, in some embodiments the channel may have a constant width along a majority of a length of the channel, the constant width being marginally wider than a width of the retractable drain.

Additionally or alternatively, in some embodiments the retractable drain may comprise a closure portion configured to seal an outlet opening of the retractable drain while in the extended configuration, and wherein the channel may have a length which is at least half the length of the retractable drain when sealed and in the extended configuration.

Additionally or alternatively, in some embodiments the guide panel may be arranged on a main body portion of the inner wall or a main body portion of the outer wall.

Additionally or alternatively, in some embodiments the guide panel may be formed from flexible sheet material, and optionally wherein the guide panel may be formed from the same material as the inner wall and/or the outer wall.

Additionally or alternatively, in some embodiments the channel may overlie the cavity such that in the retracted configuration substantially all of the retractable drain overlies the cavity.

Additionally or alternatively, in some embodiments the ostomy appliance may further comprise a comfort layer overlying at least a portion of the inner wall and/or the outer wall, wherein the ostomy appliance may comprise an opening arranged adjacent to a lower portion of the comfort layer through which the retractable drain may be moveable between the extended configuration and the retracted configuration.

Additionally or alternatively, in some embodiments the guide panel may be arranged between the inner wall or the outer wall and the comfort layer.

Additionally or alternatively, in some embodiments the channel may be aligned with the retractable drain such that the retractable drain can be slidably retracted into the channel.

The present disclosure also provides a method of storing a retractable drain of an ostomy appliance comprising the step of sliding the retractable drain into a channel arranged between a guide panel and an inner or outer wall of the ostomy appliance.

The present disclosure also provides an ostomy appliance comprising:
inner and outer walls of flexible sheet material joined together to define a cavity for containing a stomal output, the inner wall comprising an inlet for receiving the stomal output into the cavity;
a retractable drain being slidably movable between an extended configuration for draining the stomal output from the cavity and a retracted configuration for storage of the drain; and
a guide panel arranged on the inner wall or the outer wall, thereby defining a channel for receiving the retractable drain.

The channel preferably has a length sufficient such that in the retracted configuration substantially all of the retractable drain is slidably received within the channel.

Additionally or alternatively, in some embodiments in the retracted position the retractable drain may comprises a generally Z-shaped form having a first fold and a second fold, the first fold and the second fold being arranged across the retractable drain such that the first and second folds may inhibit drainage of stomal output through the retractable drain.

Additionally or alternatively, in some embodiments the first fold may be arranged across an outlet of the cavity and the second fold may be arranged such that in the retracted configuration a distal end of the retractable drain is arranged adjacent to the first fold.

The present disclosure also provides a method of storing a retractable drain of an ostomy appliance comprising the step of slidably moving the retractable drain from an extended configuration for draining the stomal output from the cavity to a retracted configuration for storage of the retractable drain;
  wherein a guide panel is arranged on the inner wall or the outer wall, thereby defining a channel for receiving the retractable drain;
  wherein the channel has a length sufficient such that in the retracted configuration substantially all of the retractable drain is slidably received within the channel.

Additionally or alternatively, in some embodiments the ostomy appliance further comprises a push element for driving the retractable drain into the channel to move the retractable drain towards the retracted configuration.

The present disclosure also provides an ostomy appliance comprising:
  inner and outer walls of flexible sheet material joined together to define a cavity for containing a stomal output, the inner wall comprising an inlet for receiving the stomal output into the cavity;
  a retractable drain being slidably movable between an extended configuration for draining the stomal output from the cavity and a retracted configuration for storage of the drain;
  a guide panel arranged on the inner wall or the outer wall, thereby defining a channel for receiving the retractable drain.
  A push element is preferably attached to an intermediate portion of the retractable drain, the push element being configured to drive at least a portion of the retractable drain into the channel to slide the retractable drain into the retracted configuration.

Additionally or alternatively, in some embodiments the push element may be attached to the retractable drain at an intermediate point on the retractable drain, wherein the intermediate point is preferably approximately halfway along a length of the retractable drain when the retractable drain is in the extended configuration with an outlet opening sealed.

Additionally or alternatively, in some embodiments a lower portion of the push element may be attached to the retractable drain at the intermediate point, and an upper portion of the push element may not be attached to the retractable drain.

Additionally or alternatively, in some embodiments at least a free end of the push element may be received in the channel when the retractable drain is in the extended configuration.

Additionally or alternatively, in some embodiments the push element may be at least partially formed from a rigid material having higher rigidity than the flexible sheet material; and optionally wherein the push element comprises an elongate strip of the rigid material.

Additionally or alternatively, in some embodiments an attachment may be provided between the push element and the retractable drain.

Additionally or alternatively, in some embodiments the push element may be attached to the retractable drain at a plurality of points or continuously along the retractable drain between an upper limit of the attachment and a lower end of the push element.

Additionally or alternatively, in some embodiments an upper end of the push element may extend upwards from the attachment away from the lower end of the retractable drain, and preferably wherein the upper end is at least partially still received within the channel when the drain is in the extended configuration.

Additionally or alternatively, in some embodiments the guide panel may be arranged on an outer face of the inner wall or an outer face of the outer wall.

Additionally or alternatively, in some embodiments the ostomy appliance further comprises a comfort layer, wherein the guide panel may comprise a portion of the comfort layer.

Additionally or alternatively, in some embodiments the guide panel may be attached by welds or adhesive to form edges of the channel, thereby providing a guide for the push element.

Additionally or alternatively, in some embodiments the guide panel may be formed from a flexible sheet material, and preferably from the same material as the inner and/or outer wall.

Additionally or alternatively, in some embodiments a mouth of the channel may be arranged adjacent to a lower part such as a lower apex of the cavity and preferably the retractable drain is configured to be pushed upwards into the channel through the mouth of the channel.

Additionally or alternatively, in some embodiments the channel may have a constant width along a majority of a length of the channel, the constant width being marginally wider than a width of the retractable drain.

Additionally or alternatively, in some embodiments the push element may extend across substantially all of a width of the retractable drain, such that the push element is slidably received within the channel along a direction aligned with an elongate axis of the retractable drain in the extended configuration.

Additionally or alternatively, in some embodiments the channel may have a depth configured such that the retractable drain is a tight sliding fit in the channel in the depth direction when the retractable drain is in the retracted configuration.

Additionally or alternatively, in some embodiments the ostomy appliance further comprises a first fastener element for fastening an outlet end of the drain in a closed position, wherein the first fastener may be arranged between the outlet end of the drain and the proximal limit of the attachment between the push element and the drain when the drain is in the extended configuration.

Additionally or alternatively, in some embodiments a lower portion of the guide panel may extend downwards from the channel, the lower portion of the guide panel being attached to an intermediate portion of the push element, and optionally wherein the lower portion of the guide panel is attached to the push element across a majority of the width of the retractable drain.

Additionally or alternatively, in some embodiments the ostomy appliance further comprises a comfort layer, wherein a lower portion of the guide panel may be arranged adjacent to the mouth of the channel, the lower portion of the guide panel being attached to the comfort layer.

The present disclosure also provides a method of storing a retractable drain of an ostomy appliance comprising the steps of:
- pushing a push element arranged on the retractable drain to drive at least a portion of the retractable drain into a channel arranged between a guide panel and an inner wall or an outer wall of the ostomy appliance.

The present disclosure also provides a method of draining an ostomy appliance comprising a retractable drain, the method comprising the steps of:
- pulling a push element arranged on the retractable drain to draw at least a portion of the retractable drain out of a channel arranged between a guide panel and an inner wall or an outer wall of the ostomy appliance.

The present disclosure also provides an ostomy appliance comprising:
- inner and outer walls of flexible sheet material joined together to define a cavity for containing a stomal output, the inner wall comprising an inlet for receiving the stomal output into the cavity;
- a retractable drain being slidably movable between an extended configuration for draining the stomal output from the cavity and a retracted configuration for storage of the drain;
- an inner comfort layer arranged over at least a part of the inner wall; and
- an outer comfort layer arranged over at least a part of the outer wall;
- wherein in the retracted configuration the retractable drain is received in a channel arranged between either the inner wall and the inner comfort layer or the outer wall and the outer comfort layer, the dimensions of the channel being configured such that the retractable drain is slidably held in the channel when in the retracted configuration;
- wherein the inner comfort layer and/or the outer comfort layer defines an opening through which the retractable drain is slidably moveable between the extended and retracted configurations; and
- wherein a closure for closing the opening is arranged at or proximal to a lower end of the channel such that the closure restricts sliding of the retractable drain from the retracted configuration.

Additionally or alternatively, in some embodiments the closure may comprise a first closure element arranged on the inner comfort layer and a second closure element arranged on the outer comfort layer.

Additionally or alternatively, in some embodiments the ostomy appliance may further comprise a guide panel arranged on an outer face of the inner wall or an outer face of the outer wall; wherein the channel may be defined between the guide panel and the inner wall or the outer wall; and wherein a lower portion of the guide panel may be arranged adjacent to the opening of the channel, the lower portion of the guide panel being attached to the comfort layer.

Additionally or alternatively, in some embodiments the lower portion of the guide panel may be attached to the closure such that opening of the closure widens a lower portion of the channel.

Additionally or alternatively, in some embodiments the channel may be defined between the guide panel and the inner wall or the outer wall.

Additionally or alternatively, in some embodiments a lower portion of the guide panel may extend downwards from the channel, the lower portion of the guide panel being attached to an intermediate portion of the push element, and optionally wherein the lower portion of the guide panel is attached to the push element across a majority of the width of the retractable drain.

Additionally or alternatively, in some embodiments the comfort layer closure may be independent of the push element.

Additionally or alternatively, in some embodiments the opening may comprise a gap in a peripheral join attaching the inner comfort layer to the outer comfort layer, wherein the join is preferably formed by welding or adhesive.

The present disclosure also provides a method of storing a retractable drain of an ostomy appliance comprising the steps of:
- sealing an outlet opening of the retractable drain;
- sliding the retractable drain through a comfort layer opening into a retracted configuration in which the retractable drain is slidably held in a channel;
- restricting sliding of the retractable drain from the retracted configuration by closing the closure.

The present disclosure also provides a method of draining an ostomy appliance comprising a retractable drain, the method comprising the steps of:
- unfastening a closure of an opening of the ostomy appliance;
- sliding the retractable drain through the opening from a retracted configuration to an extended configuration; and
- unsealing an outlet end of the retractable drain.

The present disclosure also provides an ostomy appliance comprising:
- inner and outer walls of flexible sheet material joined together to define a cavity for containing a stomal output, the inner wall comprising an inlet for receiving the stomal output into the cavity;
- a retractable drain being slidably movable between an extended configuration for draining the stomal output from the cavity and a retracted configuration for storage of the drain;
- wherein the drain comprises a closure portion which may be turned up to close (e.g. comprising a folding portion which is foldable to close) an outlet opening of the drain and a first fastener configured to fasten the folding portion in place once turned up (e.g. after folding).

The first fastener preferably comprises a pull tab for gripping by the user to slide the retractable drain from the retracted configuration to the extended configuration.

Additionally or alternatively, in some embodiments the first fastener may further comprise a first fastening element for attachment to a second fastening element to fasten the folding portion in place, the second fastening element being arranged on the retractable drain.

Additionally or alternatively, in some embodiments the first fastener may comprise:
- a first flange attached to the intermediate portion of the retractable drain adjacent to the folding portion; and
- a second flange comprising the first fastening element;

wherein the folding portion preferably further comprises the second fastening element for attachment to the first fastening element.

Additionally or alternatively, in some embodiments the first fastener may be arranged across the width of the retractable drain.

Additionally or alternatively, in some embodiments a distal end of the second flange may comprise the pull tab.

Additionally or alternatively, in some embodiments the first fastener may be attached to the retractable drain at a first fastener attachment and the second flange extends from a proximal limit of the first fastener attachment towards the outlet end of the retractable drain.

Additionally or alternatively, in some embodiments a length of the second flange may be configured such that when the folding portion is unfolded, the pull tab does not extend to the outlet opening of the retractable drain, and when the folding portion is folded, the pull tab extends beyond a lower end of the retractable drain.

Additionally or alternatively, in some embodiments the folding portion may comprise a plurality of segments having approximately equal segment lengths and separated by fold lines, and wherein the length of the second flange may be longer than the segment lengths.

Additionally or alternatively, in some embodiments the length of each of the plurality of segments may be defined by one or more pursing strips arranged on the retractable drain.

Additionally or alternatively, in some embodiments the folding portion may be configured to be foldable a plurality of times, each fold comprising folding an end portion of the retractable drain forwards and upwards to overlie the adjacent portion of the retractable drain.

Additionally or alternatively, in some embodiments at least a part of the first fastener may be arranged on an intermediate portion of the retractable drain such that the fastener is adjacent to or overlaps the folding portion.

Additionally or alternatively, in some embodiments the first fastener may comprise a flexible sheet material, wherein the flexible sheet material is preferably more rigid than the flexible sheet material of the inner and/or outer wall.

Additionally or alternatively, in some embodiments the first fastener may be arranged on a lower half of the retractable drain.

The present disclosure also provides a method of draining an ostomy appliance comprising;
pulling on a pull tab arranged on a first fastener of an ostomy appliance to slide a retractable drain of the ostomy appliance from an extracted configuration to an extended configuration.

The ostomy appliance of the present disclosure may beneficially require less dexterity for extension and retraction of the retractable drain than previous appliances, for example because the retractable drain may be pushed into the retracted configuration in a sliding motion.

The ostomy appliance of the present disclosure may beneficially avoid accidental unsealing. The closure portion may be turned upwards and fastened in place by the first fastener which extends or folds down towards the outlet end. Pulling down on the pull tab arranged on the first fastener may therefore be less likely to accidentally undo the fastening. The retractable drain may therefore stay sealed more easily while sliding into the extended configuration. The user can then unfasten and unfold or otherwise open out the outlet end when ready.

The ostomy appliance of the present disclosure may beneficially allow for the retractable drain to be fully enclosed within or behind at least one comfort layer when in the retracted configuration. There may therefore be a reduced chance of accidental movement of the retractable drain and/or inadvertent movement of the sealing folds when the ostomy appliance is being worn by the user.

Beneficially, sealing the outlet end before retraction may allow for the outlet to be securely sealed quickly, and remain reliably fastened in the sealed configuration during retraction of the retractable drain. Similarly, keeping the outlet end sealed while extending it from the retracted configuration to the extracted configuration may avoid inadvertent outflow of stomal output from the outlet end during extension, until the user is ready to open the outlet end.

The configuration of the ostomy appliance of the present disclosure may provide for a pull tab for use in extending the retractable drain to be easily kept clean, as the pull tab may be configured to be distanced from the outlet end while the outlet end is open for drainage of the stomal output.

BRIEF DESCRIPTION OF THE DRAWINGS

One or more embodiments of the disclosure will now be described, by way of example only, with reference to the accompanying drawings in which:

FIGS. 9a to 9c schematically illustrate a cross-section of the ostomy appliance of FIG. 1 with the retractable drain in a) the extended configuration b) the extended configuration with the closure portion folded and fastened and c) a partial view in the retracted configuration.

DETAILED DESCRIPTION OF THE DISCLOSURE

Figure 1:
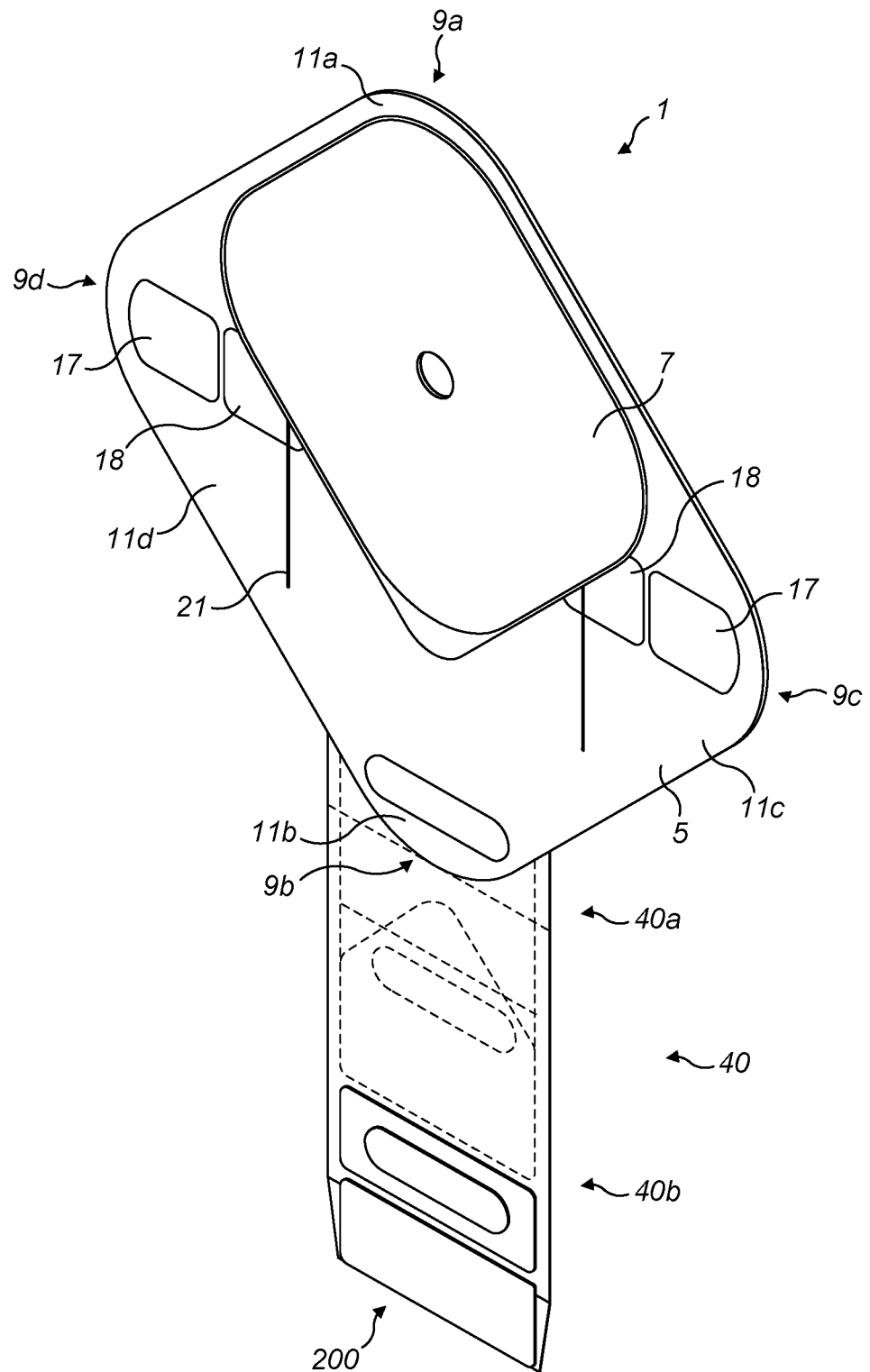
FIG. 1 illustrates a schematic perspective view of an embodiment of ostomy appliance according to the present disclosure in the extended configuration with the closure portion unfastened and unfolded.

In the following description, the equivalent reference numerals are used in different embodiments to denote equivalent or similar features.

Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

In this specification, the use of the singular includes the plural unless the context clearly dictates otherwise. In this specification, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

Figure 2:
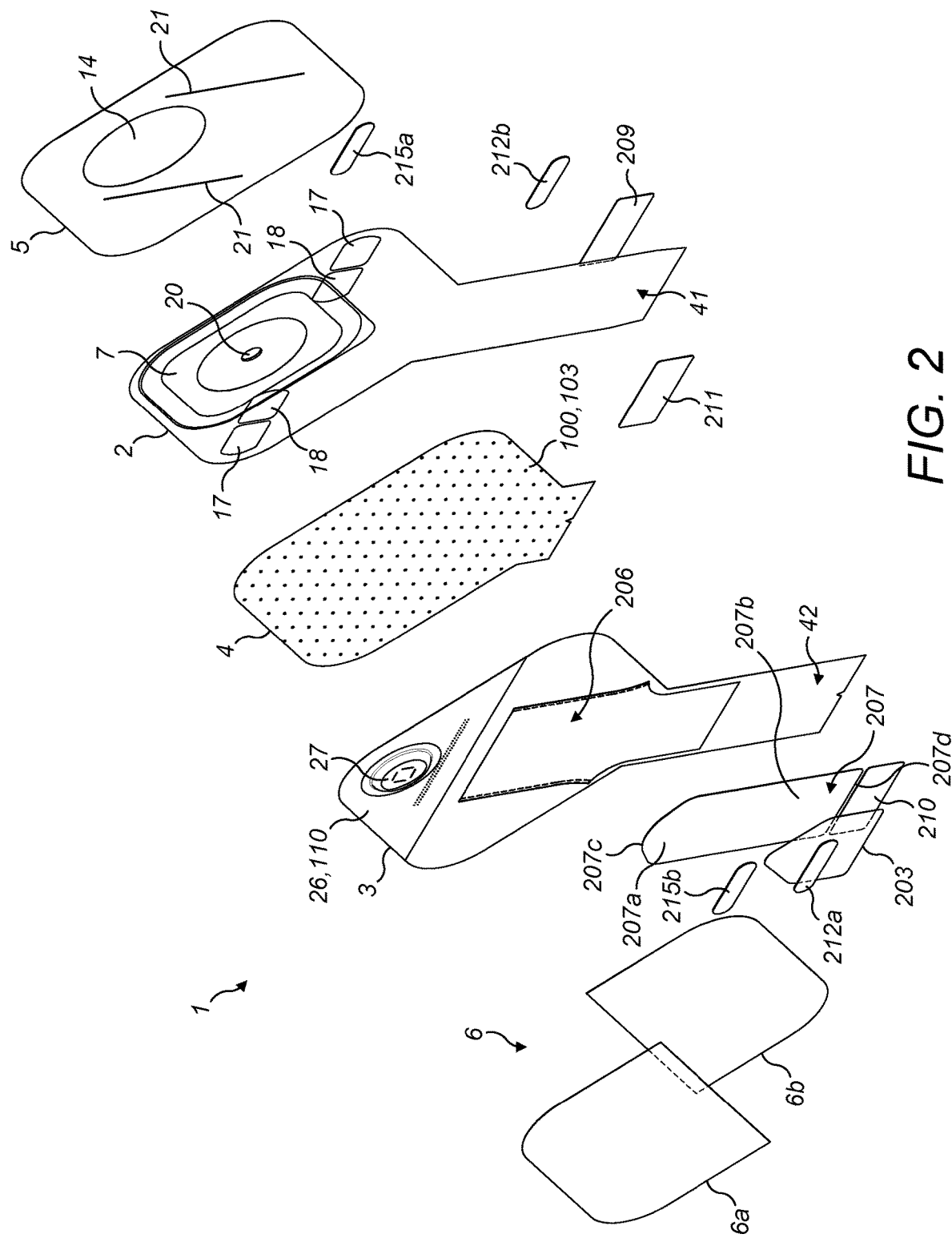
FIG. 2 illustrates a schematic exploded perspective view of components of the ostomy appliance of FIG. 1.

A first example embodiment of an ostomy appliance 1 according to the present disclosure is shown in FIGS. 1 to 9. As shown in FIGS. 1 and 2, the ostomy appliance 1 may generally comprise an inner wall 2, an outer wall 3, a separation wall 4, an inner comfort layer 5, an outer comfort layer 6 and an ostomy wafer 7. The ostomy appliance 1 of this example is a one-piece appliance wherein the ostomy wafer 7 is permanently attached to the ostomy appliance 1, to the extent that the ostomy wafer 7 cannot easily be separated without risk of damaging the ostomy appliance 1. However, the teachings of this disclosure may also be applied, with suitable alteration where necessary, to a two-piece appliance. For example, where the ostomy appliance 1 is a two-piece appliance the inner wall 2, the outer wall 3, the separation wall 4, the inner comfort layer 5 and the outer comfort layer 6 may together form a pouch appliance that in use may be coupled to a body fitment component that comprises the ostomy wafer 7.

The inner wall 2 and the outer wall 3 are joined together to define a cavity for containing a stomal output. The inner wall 2 and the outer wall 3 are of flexible sheet material.

Figure 3:
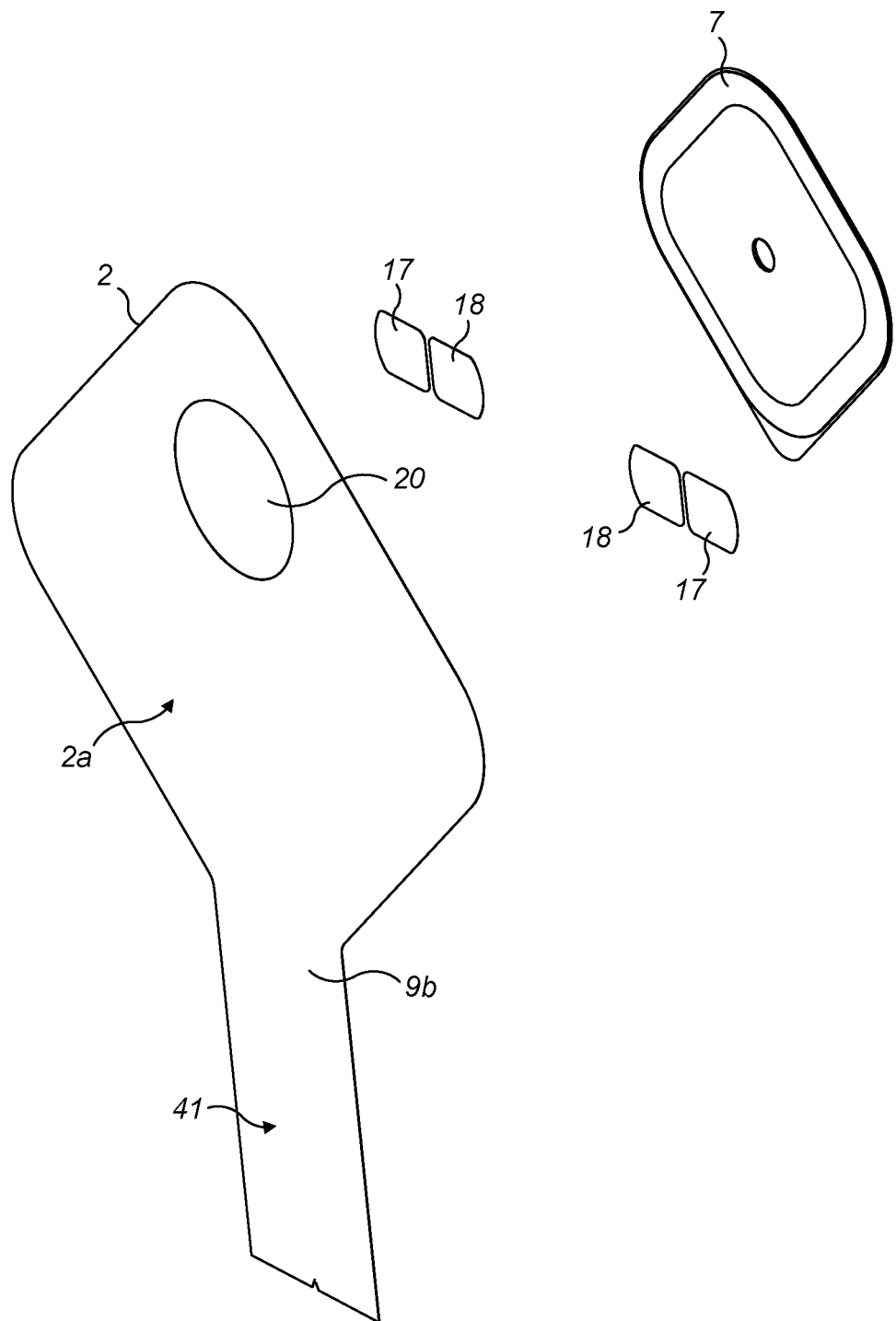
FIG. 3 illustrates a schematic exploded perspective view of some of the components of the ostomy appliance of FIG. 1.

As shown in FIGS. 2 and 3, the inner wall 2 is provided with a stomal inlet 20 for receiving the stomal output into the cavity. The stomal inlet 20 may be an aperture that is stamped or cut out of the inner wall 2.

The ostomy appliance 1 is configured as an open appliance and further comprises a retractable drain 40. FIGS. 1 to 6 show the retractable drain 40 in an extended configuration.

In this specification an "open appliance" refers to an appliance where it is intended that stomal output is drained from the cavity. Thus, an open appliance may be configured as a reusable appliance, such that it can be reused and emptied multiple times whilst attached to the body, although this is not essential. In an open appliance the stomal output may be drained intermittently as instigated by an action of the ostomate or may be drained intermittently or continuously due to the cavity being fluidly connected to a drain, for example a night drain line.

Figure 5:
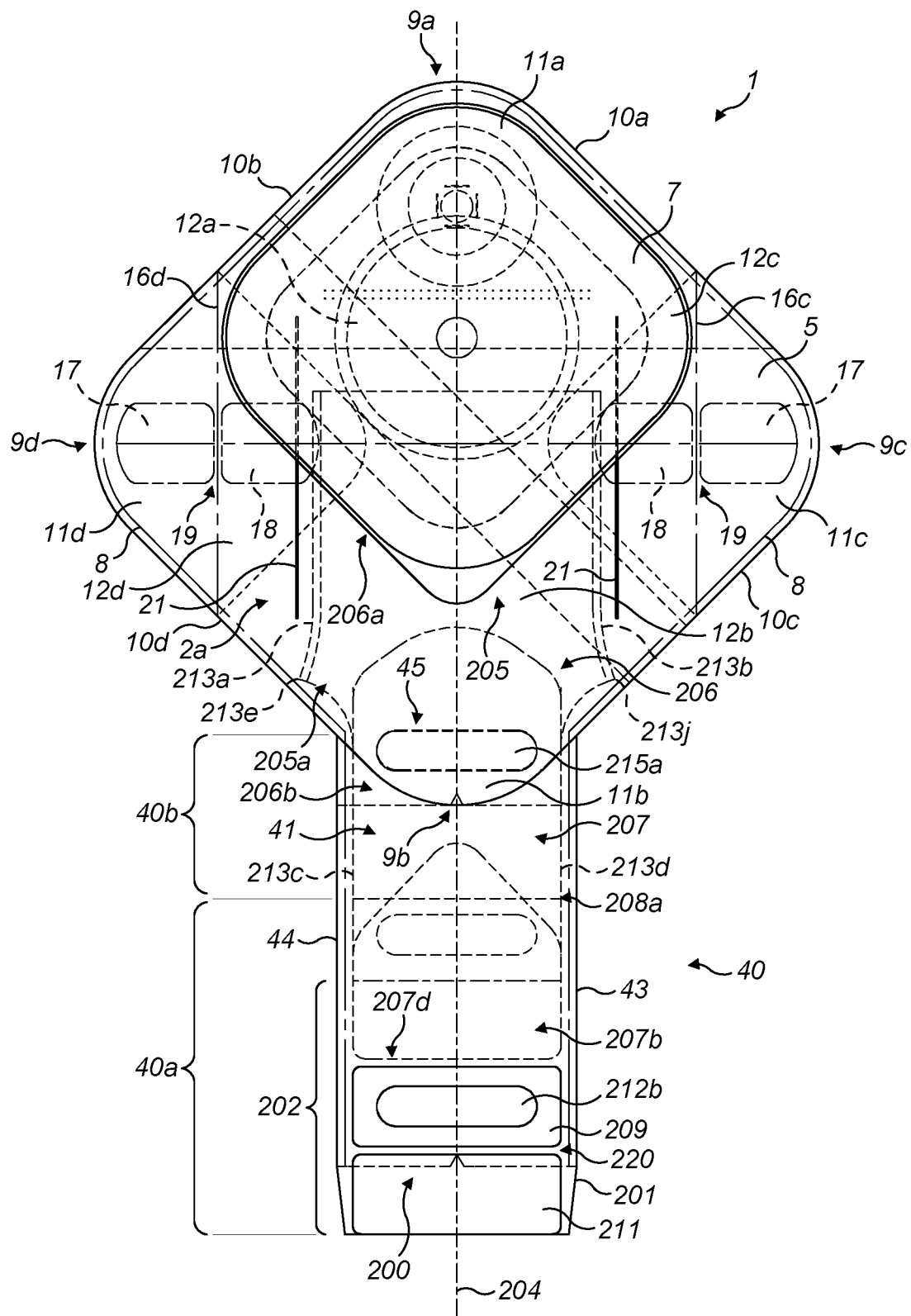
FIG. 5 illustrates a schematic rear view of the ostomy appliance of FIG. 1.

The retractable drain 40 may take the general form of an elongate extension of the inner wall 2 and the outer wall 3 that together define an elongate drain passage that extends from the cavity to an outlet opening 200 located at a lower end of the retractable drain as shown in FIG. 5.

Figure 4:
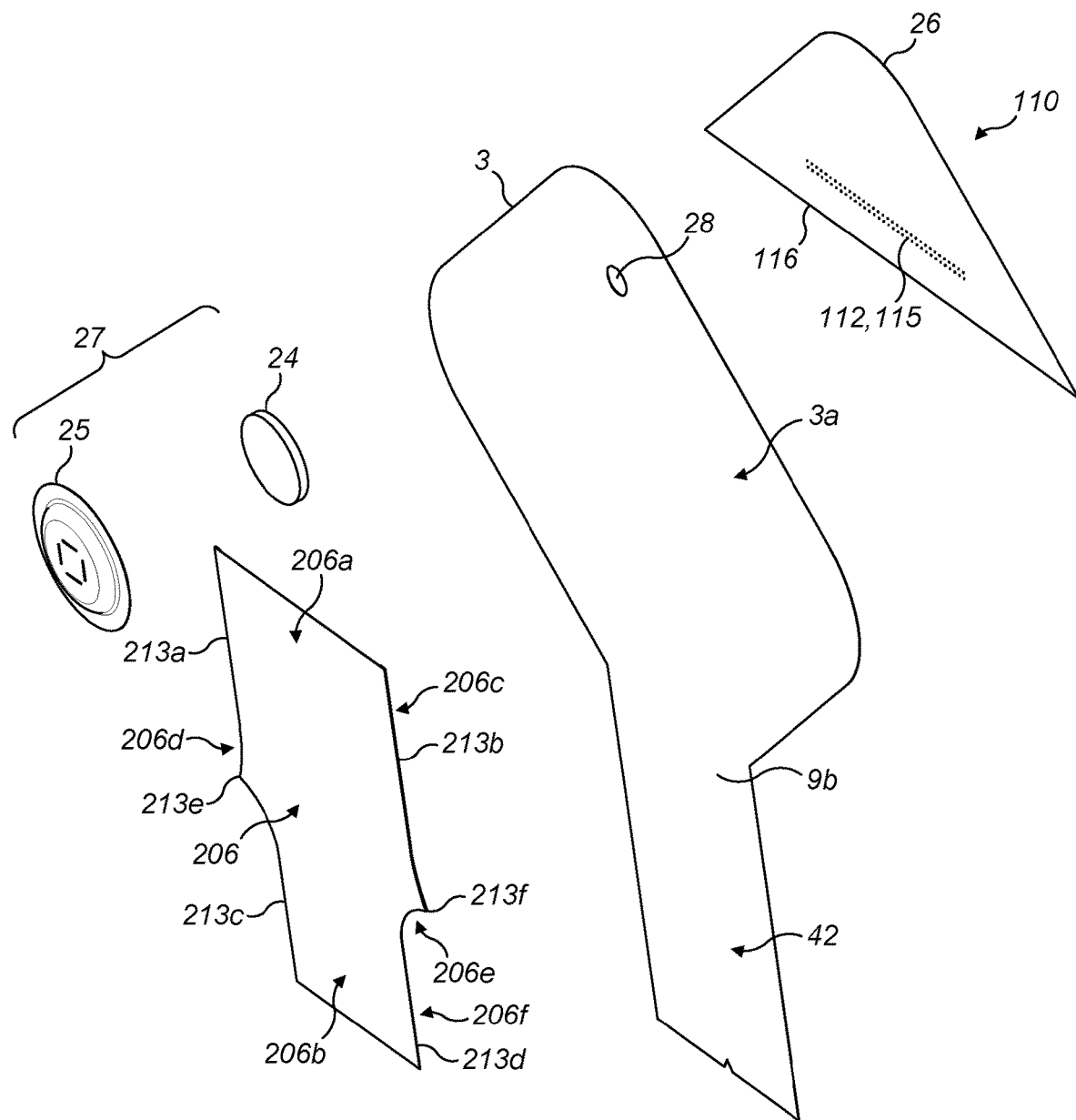
FIG. 4 illustrates a schematic exploded perspective view of some further components of the ostomy appliance of FIG. 1.

As shown in FIG. 3, the inner wall 2 may comprise a main body portion 2a and an inner drain portion 41. Likewise, as shown in FIG. 4, the outer wall 3 may comprise a main body portion 3a and an outer drain portion 42. The inner drain portion 41 may extend from the main body portion 2a of the inner wall 2. The outer drain portion 42 may extend from the main body portion 3a of the outer wall 3. The inner drain portion 41 and the main body portion 2a may be formed from the same, integral, sheet of flexible sheet material, for example by cutting or stamping them out of sheet material as a single part. Likewise, the outer drain portion 42 and the main body portion 3a may be formed from the same, integral, sheet of flexible sheet material, for example by cutting or stamping them out of sheet material as a single part.

The main body portions 2a, 3a may be a quadrilateral-shaped portions. For example, the main body portions 2a, 3a may each be a diamond-shaped portion, a rhombus-shaped portion, or a square-shaped portion.

The main body portions 2a, 3a of the inner wall 2 and outer wall 3 may be joined together around their peripheral edges by use of welding, adhesive or equivalent means. Welding is a preferred method of joining the inner wall 2 and the outer wall 3. As shown in FIG. 5, a peripheral weld 8 may extend around at least a portion of the perimeter of the main body portions 2a, 3a of the inner wall 2 and the outer wall 3 to create a fluid-tight seal there between. The peripheral weld 8 may have a width of 1 to 3 mm, preferably about 2 mm.

Preferably the retractable drain 40 extends from at or near a lower apex 9b of the main body portions 2a, 3a as shown in FIG. 5.

The inner drain portion 41 and/or the outer drain portion 42 may be generally rectangular along the majority of their length.

Figure 6:
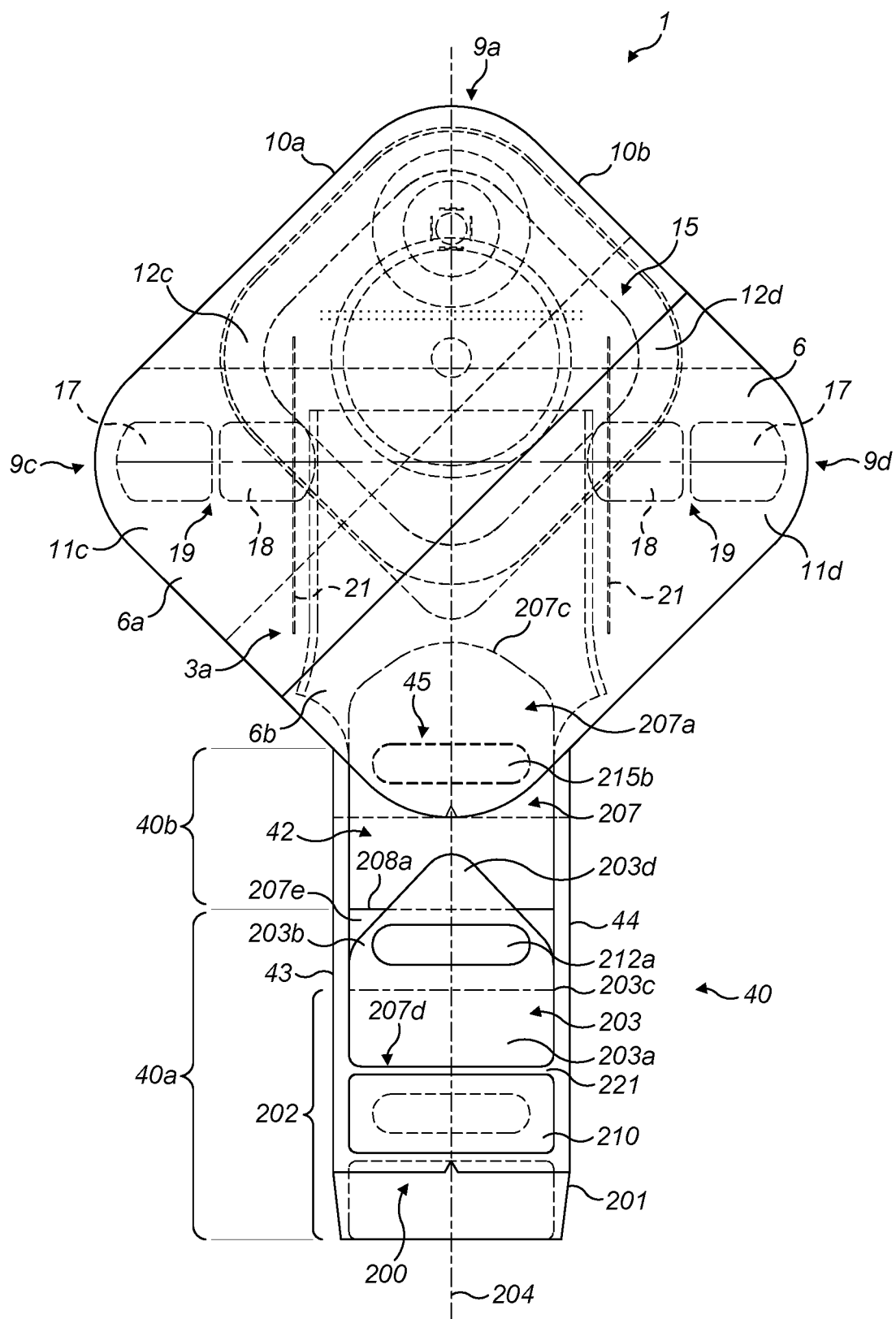
FIG. 6 illustrates a schematic front view of the ostomy appliance of FIG. 1.

Lateral edges 43, 44 of the retractable drain 40 may be generally parallel to each other, such that the retractable drain 40 has a constant width along a majority of its length, and optionally along all of its length. The inner drain portion 41 may extend further from the cavity (i.e. have a longer length) than the outer drain portion 42, forming a lip 201 at the outlet opening 200 of the retractable drain 40 as shown in FIGS. 5 and 6.

The outer and/or inner drain portion 41, 42 may have converging sides at their lower ends adjacent the outlet opening 200. In the illustrated example of FIG. 5 the lateral edges 43, 44 are parallel along their length and the lip 201 has a tapered shape.

The inner drain portion 41 may be joined to the outer drain portion 42 at their respective lateral edges 43, 44 to form a fluid tight seal. The join may be formed by use of welding, adhesive or equivalent means. Welding is a preferred method of joining the inner drain portion 41 and the outer drain portion 42.

The joins between the inner drain portion 41 and the outer drain portion 42 may preferably comprise a continuation of the peripheral join extending around the main body portions 2a, 3a. For example, the peripheral weld 8 may start adjacent to the outlet opening 200 on a left hand side of the ostomy appliance 1 (as viewed in FIG. 5) and extend as a continuous weld up the lateral edge 43, clockwise around the four sides of the main body portions 2a, 3a and down the lateral edge 44 to a point adjacent to the outlet opening 200 on a right hand side of the ostomy appliance 1 (as viewed in FIG. 5).

Communication between the cavity and the elongate drain passage may be via a drain inlet 45 that may be defined as the point of transition between the cavity and the retractable drain 40. The drain inlet 45 may function to allow passage of stomal output from the cavity into the retractable drain 40 when the retractable drain 40 is in the extended configuration. The outlet opening 200 may to allow outflow of the stomal output from the retractable drain 40 when the retractable drain 40 is in the extended configuration.

In the illustrated example of FIG. 2, the inner comfort layer 5 overlies the inner wall 2 and the outer comfort layer 6 overlies the outer wall 3.

The inner comfort layer 5 and the outer comfort layer 6 may be formed of a flexible sheet material. The flexible sheet material may comprise a fabric layer. The fabric layer may be a textile layer. The textile layer may be a woven or a non-woven textile layer. Examples of suitable materials include one or more of polyester, nylon, viscose, polyethylene and polypropylene.

The inner comfort layer 5 and the outer comfort layer 6 may comprise at least one fabric layer and at least one film layer. The at least one fabric layer may comprise a non-woven textile layer but is preferably a woven textile layer. The woven textile layer may comprise one or more of polyester, nylon, viscose, polyethylene and polypropylene. The film layer may comprise one or more of polyurethane, polyethylene (PE), polyvinylidene chloride (PVDC) and ethylene-vinyl acetate (EVA). The at least one film layer may be laminated to the at least one fabric layer, and optionally may be laminated to the at least one fabric layer over an entire area of the inner comfort layer 5 and the outer comfort layer 6.

The inner comfort layer 5 may overlie the inner wall 2. The inner comfort layer 5 may cover only a portion of the inner wall 2, for example at least the main body portion 2a. The inner comfort layer 5 may cover all of the inner wall 2 (except for the stomal inlet 20 of the inner wall 2).

The inner wall 2 and the inner comfort layer 5 may be joined together around their peripheral edges by use of welding, adhesive or equivalent means.

As shown in FIG. 5, a peripheral weld may extend around at least a portion of the perimeter of the inner wall 2 and the inner comfort layer 5. The peripheral weld may extend around the four sides of the inner comfort layer 5. The peripheral weld that joins the inner wall 2 with the inner comfort layer 5 may be the whole or a portion of the peripheral weld 8 that joins the inner wall 2 and the outer wall 3.

As shown in FIG. 2, the inner comfort layer 5 is preferably provided with a wafer aperture 14 that is in register with the stomal inlet 20 of the inner wall 2.

The outer comfort layer 6 overlies at least a portion of the outer wall 3, for example at least the main body portion 3a. The outer wall 3 and the outer comfort layer 6 may be joined together around their peripheral edges by use of welding, adhesive or equivalent means. A peripheral weld may extend around at least a portion of the perimeter of the outer wall 3 and the outer comfort layer 6. The peripheral weld may extend around the four sides of the outer comfort layer 6. The peripheral weld that joins the outer wall 3 with the outer comfort layer 6 may be the whole or a portion of the peripheral weld 8 that joins the inner wall 2 and the outer wall 3.

In some embodiments, the peripheral weld 8 may be one weld that joins together the inner comfort layer 5, the inner wall 2, the outer wall 3 and the outer comfort layer 6.

The main body portions 2a, 3a of the inner wall 2 and the outer wall 3 may be quadrilateral in shape when the inner wall 2 and the outer wall 3 are in an unfolded configuration as show in FIGS. 5 and 6. Preferably, the inner comfort layer 5 and the outer comfort layer 6 are also quadrilateral in shape when in an unfolded configuration as show in FIGS. 5 and 6. Preferably, in the unfolded configuration the main body portions 2a, 3a of the inner wall 2 and the outer wall 3 are flat or substantially flat. The figures illustrate a preferred example wherein the main body portions 2a, 3a of the inner wall 2, the outer wall 3, the inner comfort layer 5 and the outer comfort layer 6 are square in shape in the unfolded configuration. The main body portions 2a, 3a of the inner wall 2 and outer wall 3 may have a length of 120 mm to 200 mm, preferably 140 mm to 160 mm, for example 145 mm. The main body portions 2a, 3a of the inner wall 2 and outer wall 3 may have a width of 120 mm to 200 mm, preferably 140 mm to 160 mm, for example 145 mm. The inner comfort layer 5 and the outer comfort layer 6 may have the same external shape and dimensions as the main body portions 2a, 3a of the inner wall 2 and the outer wall 3 so that the main body portions 2a, 3a of the inner wall 2 and the outer wall 3 are preferably covered up to their edges.

The main body portions 2a, 3a of the inner wall 2 and the outer wall 3 may have one or more rounded apexes 9. All of the apexes 9 may be rounded. It is preferred that the main body portions 2a, 3a of the inner wall 2 and the outer wall 3 have three or four rounded apexes 9. The radius of curvature of each rounded apex 9 may be about 30 mm.

When in use (i.e. when worn by an ostomate) the main body portions 2a, 3a of the inner and outer walls 2, 3 may comprise an upper apex 9a which points generally vertically upwards, the lower apex 9b (from which the retractable drain 40 extends) which points generally vertically downwards and opposed lateral apexes 9c, 9d which point generally to each side, as shown by way of example in FIG. 5. The upper apex 9a may be joined to the opposed lateral apexes 9c, 9d by first and second edges 10a, 10b and the lower apex 9b may be joined to the opposed lateral apexes 9c, 9d by third and fourth edges 10c, 10d. In this configuration the main body portions 2a, 3a of the inner wall 2 and the outer wall 3 may be considered to be 'diamond-shaped'. One or more of the upper apex 9a, the lower apex 9b and the opposed lateral apexes 9c, 9d may be rounded, for example as described above.

One or more of the first, second, third and fourth edges 10a-d may be straight, i.e. the edge 10a-d may be straight from a first apex at one end of the edge to a second apex at an opposite end of the edge. Where the apex 9 is rounded, the edge 10a-d may be straight between the rounded apex(es) 9.

The inner comfort layer 5 and the outer comfort layer 6 may define an opening 130 therebeween as shown in FIG. 9b through which the retractable drain 40 is moveable between the extended configuration and the retracted configuration. The ostomy appliance 1 may comprise a closure 215 for closing the opening 130, the closure 215 being operable to retain the retractable drain 40 when the retractable drain 40 is in the retracted configuration. The closure 215 may comprise a first closure element 215a arranged on the inner comfort layer 5 and a second closure element 215b arranged on the outer comfort layer 6. The first closure element 215a and the second closure element 215b may comprise any suitable fastener elements, for example hook-and-loop type fastener elements.

The outer comfort layer 6 may comprise multiple parts. The external shape and dimensions of the multiple parts when taken together may be the same as that of the outer wall 3, or at least the main body portion 3a of the outer wall 3. For example, the outer comfort layer 6 may comprise a first part 6a and a second part 6b which may be joined to the main body portion 3a of the outer wall 3 so that the first part 6a partially overlaps the second part 6b in an overlap region 15 as shown in FIG. 6. The first part 6a and the second part 6b may be separable from each other in the overlap region 15 to form a window opening for viewing the cavity. The overlap region 15 may extend obliquely from at or near a mid-point of the first edge 10a to at or near a mid-point of the fourth edge 10d. Alternatively, the overlap region 15 may extend obliquely from at or near a mid-point of the second edge 10b to at or near a mid-point of the third edge 10c. In another alternative the overlap region 15 may extend horizontally when the ostomy appliance 1 is in use.

As shown in FIGS. 5 and 6, the main body portions 2a, 3a of the inner wall 2 and the outer wall 3 may comprise at least one peripheral region 11a-d which may be configured to be folded in use between a folded configuration and an unfolded configuration. The main body portions 2a, 3a of the inner wall 2 and the outer wall 3 may comprise more than one peripheral region 11a-d, for example, two or three peripheral regions 11a-d.

The at least one peripheral region 11a-d may have a substantially triangular shape with a free edge that comprises the apex 9. The upper apex 9a may be in an upper peripheral region 11a and the opposed lateral apexes 9c, 9d may be in left and right peripheral regions 11d, 11c as shown in FIG. 5.

The at least one peripheral region 11a-d may comprise at least one lateral wing region and preferably comprises at least two lateral wing regions 11c, 11d, for example being the left and right peripheral regions 11d, 11c. The at least one lateral wing region 11c, 11d may each comprise an apex 9c, 9d that is pointed sideways when the ostomy appliance 1 is in use.

According to the present disclosure the main body portions 2a, 3a of the inner wall 2 and the outer wall 3 may comprise at least one adjacent region 12a-d. Each of the peripheral regions 11a-d may be located next to an adjacent region 12a-d. A dedicated adjacent region 12a-d may be provided for each peripheral region 11a-d. Alternatively, an adjacent region 12a-d may be adjacent more than one peripheral region 11a-d. The one or more adjacent regions 12a-d may be located towards or in a central region of the main body portions 2a, 3a of the inner wall 2 and the outer wall 3.

In the illustrated example two peripheral regions 11c, 11d are provided—a left lateral wing region 11d (as viewed in FIG. 5) and a right lateral wing region 11c. In this example two adjacent regions 12a-d are provided, one next to each of the left and right lateral wing regions—a left adjacent region 12d and a right adjacent region 12c.

Each peripheral region 11a-d may be foldable about a fold line that extends between the peripheral region 11a-d and its adjacent region 12a-d. The at least one lateral wing region 11c, 11d may be foldable about a fold line 16c, 16d that extends in a generally vertical direction when the ostomy appliance 1 is in use.

The flexible sheet material of the inner wall 2 and the outer wall 3 may be formed of polyurethane, polyethylene (PE), polyvinylidene chloride (PVDC) and/or ethylene-vinyl acetate (EVA). The flexible sheet material may have a thickness of 50 to 150 micrometres, preferably 75 to 100 micrometres.

As shown in FIGS. 1 to 3, the at least one peripheral region 11a-d may comprise a stiffening member 17. Additionally or alternatively, the at least one adjacent region 12a-d may comprise a stiffening member 18. Complementary stiffening members 17, 18 may be provided on both the peripheral region 11a-d and the adjacent region 12a-d as shown in FIG. 1. Alternatively, stiffening members 18 may be provided only on the at least one peripheral region 11a-d and not on the at least one adjacent region 12a-d. In a further non-illustrated alternative, stiffening members 17 may be provided only on the at least one adjacent region 12a-d and not on the at least one peripheral region 11a-d.

The one or more stiffening members 17, 18 are preferably covered by the inner comfort layer 5 to avoid contact between the skin of the ostomate and the stiffening members 17, 18.

The stiffening members 17, 18 of the at least one peripheral region 11a-d and the at least one adjacent region 12a-d may be separated from one another and may comprise two parts. The stiffening members 17, 18 of the at least one peripheral region 11a-d and the at least one adjacent region 12a-d may be separated by a gap 19 which may define the location of folding of the at least one peripheral region 11a-d.

The stiffening members 17, 18 of the at least one peripheral region 11a-d and the at least one adjacent region 12a-d may be located equidistant from the fold line 16c-d that extends between the at least one peripheral region 11a-d and the at least one adjacent region 12a-d.

Each stiffening member 17, 18 may have a rectangular shape. Each stiffening member 17, 18 may be of the same size. The stiffening members 17, 18 may have a length of 10 to 40 mm, a width of 10 to 30 mm and a thickness of 0.25 to 1.00 mm. The stiffening members 17, 18 may be formed of one or more of polystyrene, polypropylene, polyethylene. ethylene vinyl acetate (EVA) and/or thermoplastic polyurethane (TPU).

The stiffening members 17, 18 may be integrated in, or affixed to, the main body portion 3a of the outer wall 3 but is preferably integrated in, or affixed to, the main body portion 2a of the inner wall 2. In some embodiments each stiffening member 17, 18 is adhered to the main body portion 2a of the inner wall 2 using an adhesive. The stiffening members 17, 18 may be located on an inner or an outer face of the main body portion 2a of the inner wall 2.

In the example of FIG. 2, the stiffening members 17, 18 are each a rectangular piece of polystyrene measuring 30 mm by 20 mm by 0.50 mm that is adhered to the inner wall 2

One or more openings may be provided in the inner comfort layer 5 and/or the outer comfort layer 6 which are configured to receive a portion of the at least one peripheral region 11a-d of the inner wall 2 and outer wall 3 and to releasably retain the at least one peripheral region 11a-d in its folded configuration. The one or more openings may be so configured by one or more of their location, size and orientation. In some embodiments the one or more openings are provided in the inner comfort layer 5. In the following, the one or more openings will be described as being only in the inner comfort layer 5. However, openings of the same type as described may also or alternatively be provided in the outer comfort layer 6.

The one or more openings may be slits 21 in the inner comfort layer 5. The slits 21 may be straight slits. The slits 21 may pass through the full thickness of the inner comfort layer 5. Where the inner comfort layer 5 is a laminate, the slits 21 may pass through one or more layers of the laminate. The slits 21 may be orientated vertically when the ostomy appliance 1 is in use. The slits 21 may be orientated horizontally when the ostomy appliance 1 is in use. The inner comfort layer 5 may comprise two slits 21. The two slits 21 may be located symmetrically about a vertical mid-line of the ostomy appliance 1.

The ostomy wafer 7 may be located in register with the stomal inlet 20 of the inner wall 2. The ostomy wafer 7 may extend through the wafer aperture 14 of the inner comfort layer 5. The ostomy wafer 7 may be located in the upper peripheral region 11a of the inner wall 2 and the outer wall 3. The periphery of the ostomy wafer 7 preferably does not extend beyond the periphery of the inner wall 2 and the outer wall 3 in the unfolded configuration.

The ostomy appliance 1 may be provided with a gas vent 27 for venting of stomal gases from the cavity. The ostomy appliance 1 may comprise a gas vent filter 24, which may be an odour filter, for example a charcoal or activated carbon filter, for reducing the release of unwanted odours from the cavity.

The gas vent 27 may be located, in use, in the upper half or more preferably upper quarter of the ostomy appliance 1. In particular, the centre of the at least one gas vent aperture 28 may be located, in use, above the centre of the stomal inlet 20. The gas exits the ostomy appliance 1 through the at least one gas vent aperture 28, the gas vent filter 24 and a filter cap 25.

As shown in FIG. 2, the separation wall 4 may be located between the main body portions 2a, 3a of the inner wall 2 and the outer wall 3. The separation wall 4 comprises a separation filter 100 for filtering stomal gases and/or stomal liquids from stomal solids contained in the stomal output. The separation filter 100 may thus prevent stomal solids from contacting the gas vent 27 and clogging or otherwise impairing the functionality of the gas vent filter 24.

Figure 9A:
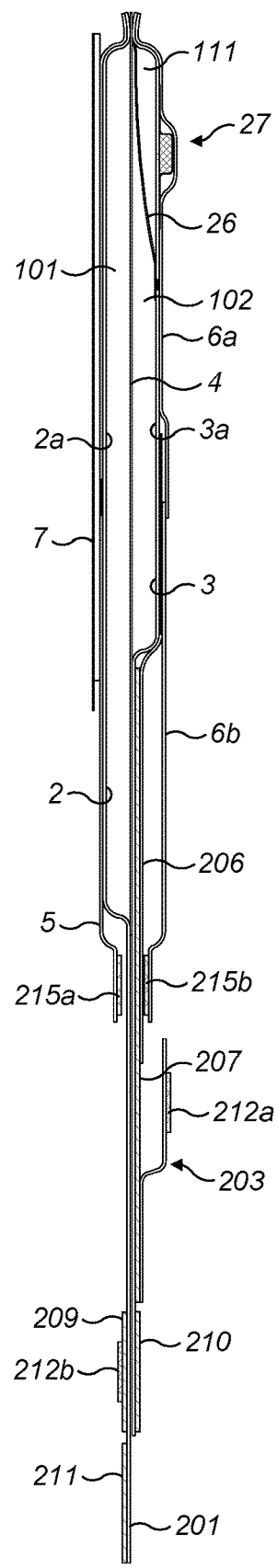

The cavity of the ostomy appliance 1 may be sub-divided into two volumes by the separation wall 4 to form first and second chambers 101, 102 as best illustrated in FIG. 9a. The first chamber 101 may extend between the separation wall 4 and the inner wall 2 and the second chamber 102 may extend between the separation wall 4 and the outer wall 3. The first and second chambers 101, 102 may have substantially the same volume or they may have different volumes. The second chamber 102 may have a larger volume than the first chamber 101.

The separation wall 4 may be joined to the inner wall 2 and outer wall 3 at or adjacent to a part or the whole of the peripheral edges of the main body portions 2a, 3a, preferably by use of welding, adhesive or equivalent means. Welding is a preferred method of joining and the peripheral weld that joins the inner wall 2, outer wall 3 and separation wall 4 may be the whole or a portion of the peripheral weld 8 that joins the inner wall 2 and the outer wall 3. As shown in FIG. 5, the welding of the separation wall 4 may extend around the four edges of the main body portions 2a, 3a. This portion of the weld may join both the inner wall 2 and the outer wall 3 to the separation wall 4. A lower portion of the separation wall 4 may extend into an upper portion of the retractable drain 40 as shown in FIG. 9. The welding of the edges of the separation wall 4 may also extend down into the retractable drain 40 to join the edges of the lower portion of the separation wall 4 to the edges of the inner wall 2 and the outer wall 3. However, the lowermost edge of the separation wall 4 is left unattached from the inner wall 2 and the outer wall 3. In this way the folding of the retractable drain 40 when moved into the retracted configuration folds the inner wall 2, outer wall 3 and the separation wall 4 such that the first and second chambers 101, 102 are sealed from each other (other than via the separation filter 100). However, the lowermost edge being unattached permits stomal output from the first chamber 101 and the second chamber 102 to enter the retractable drain 40 when the retractable drain 40 is in its extended configuration.

The separation wall 4 may comprise a flexible sheet material, which may be formed of polyurethane, polyethylene (PE), polyvinylidene chloride (PVDC) and/or ethylene-vinyl acetate (EVA). The flexible sheet material of the separation wall 4 may have a thickness of 50 to 150 micrometres, preferably 75 to 100 micrometres.

The separation wall 4 may comprise a hydrophobic and/or oleophobic coating applied to the flexible sheet material and/or the flexible sheet material may be hydrophobic and/or oleophobic.

The ostomy appliance 1 may further comprise a protective structure 110 comprising a protective panel 26 for substantially protecting the gas vent 27 from liquid located in the cavity and second chamber 102. The protective panel 26 may be attached to the outer wall 3 and more preferably the inner wall 2, outer wall 3 and separation wall 4. The protective panel 26 may define a protective chamber 111 around the gas vent 27 and the protective chamber 111 may be located within the cavity and second chamber 102. The protective structure 110 may comprise a protective chamber gas inlet 112 for allowing the stomal gas to migrate into the protective chamber 111 from the second chamber 102. The stomal gas may thus migrate through the protective chamber 111 to the gas vent 27 such that it can exit the ostomy appliance 1.

Figure 8:
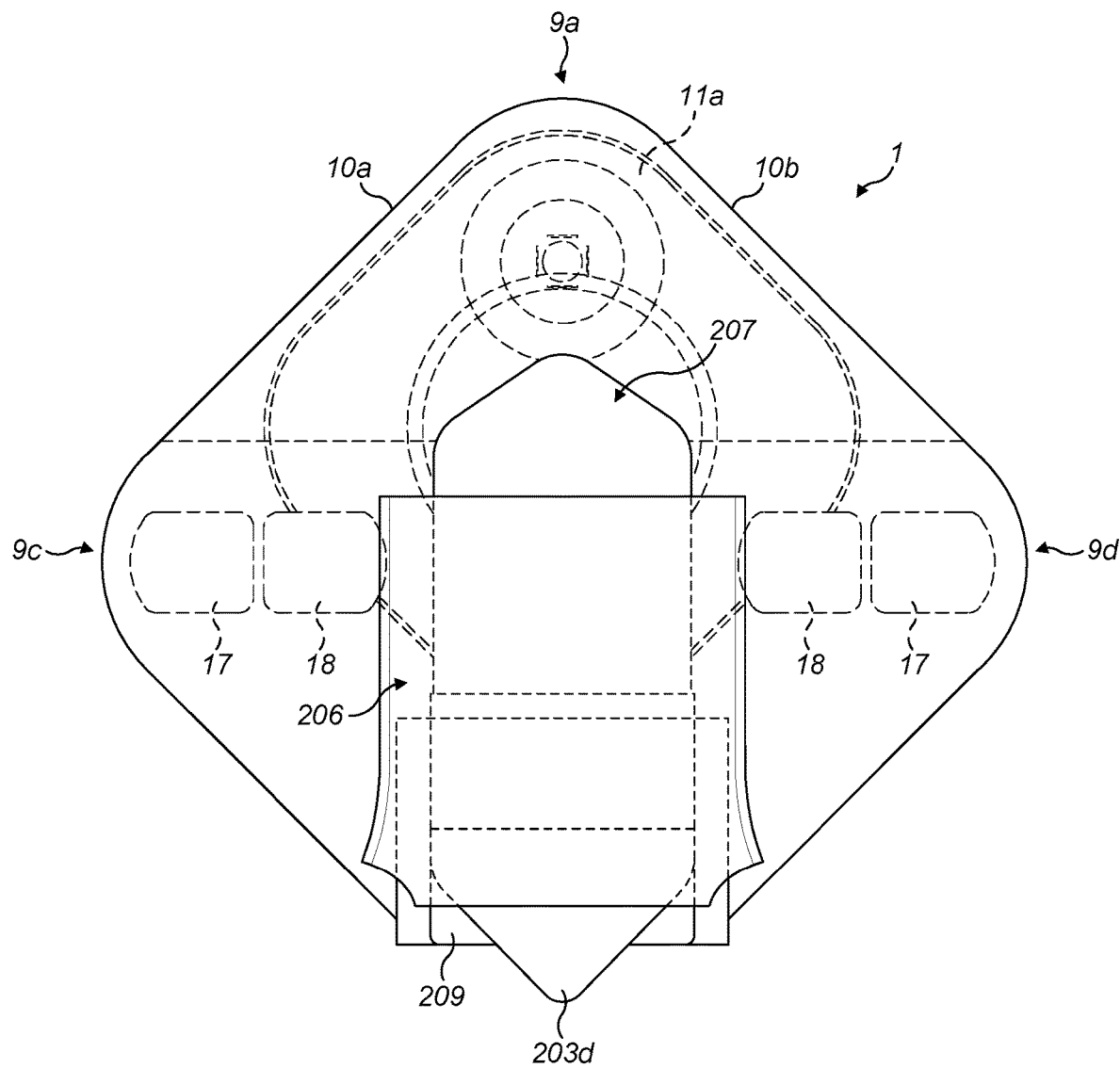
FIG. 8 illustrates a schematic view of the retractable drain of the ostomy appliance of FIG. 1 in the retracted configuration with the comfort layer omitted.

The retractable drain 40 is movable between a retracted configuration for storage, as shown in FIG. 8, and the extended configuration, as shown in FIG. 1, for draining stomal output from the cavity. In the retracted configuration the retractable drain 40 may be accommodated within the periphery of the main body portion 2a of the inner wall 2 and/or the main body portion 3a of the outer wall 3 and/or the one or more comfort layers 5, 6. The retractable drain 40 may be accommodated within a void space between the main body portion 2a of the inner wall 2 and the inner comfort layer 5 or between the main body portion 3a of the outer wall 3 and the outer comfort layer 6. Movement of the retractable drain 40 into the retracted configuration will be described in more detail below.

The retractable drain 40 may comprise a lower section 40a and an upper section 40b as shown in FIG. 5.

The retractable drain 40 may comprise a closure portion 202 which may comprise a part of the lower section 40a of the retractable drain 40. The closure portion 202 may comprise a section of the retractable drain 40 which extends up from the outlet opening 200 to an upper limit 203c as shown in FIG. 6. The length of the closure portion 202 may be from one-third to one-half of the length of the retractable drain 40.

The closure portion 202 may be configured to be folded or otherwise turned up on itself to close off the outlet opening 200 while the retractable drain 40 is in the extended configuration.

The closure portion 202 may be folded into a plurality of segments having approximately equal segment lengths and separated by folds. The closure portion 202 may therefore be successively folded one or more times such that the segments overlie each other. Preferably, the closure portion 202 may be configured to be folded to form a plurality of folds across the width of the retractable drain 40 to inhibit and preferably prevent passage of stomal output out of the outlet opening 200. For example, the segments and fold lines may have appropriate lengths and locations respectively such that the closure portion 202 can be folded or rolled repeatedly in the same sense, folding forwards and upwards towards the upper end of the retractable drain 40 with each fold. The folds may be generally perpendicular to an elongate axis 204 of the retractable drain 40 and extend across the whole width of the retractable drain 40 to close off the drain passage at each fold location.

Passage of stomal output through the closure portion 202 may initially be inhibited by folding the lip 201 over to close the outlet opening 200 of the retractable drain 40.

One or more pursing strips 209-211 may be provided on the closure portion 202. The pursing strips 209-211 may function to both provide localised rigidity to the retractable drain 40 and also to define the locations and orientations of the segments and folds of the closure portion 202.

The pursing strips 209-211 may comprise strips of material attached to the retractable drain 40. The pursing strips 209-211 may be formed from a material, preferably a flexible material, having a higher rigidity than the material of the retractable drain 40 and having some resilience such that once attached to the retractable drain 40 the pursing strips 209-211 can each be squeezed laterally to arch the pursing strip (and therefore the attached drain material) and thereby open the elongate drain passage.

As shown in FIGS. 5 and 6, a first pursing strip 209 may be attached to the inner drain portion 41. A second pursing strip 210 may be attached to the outer drain portion 42. A lip pursing strip 211 may be attached to the inner drain portion 41 below the first pursing strip 209 and adjacent to the outlet opening 200 of the retractable drain 40. Preferably, the lip pursing strip 211 may be arranged on the lip 201.

As shown in FIG. 5, a longitudinal gap 220 may be provided between a lower edge of the first pursing strip 209 and an upper edge of the lip pursing strip 211. The longitudinal gap 220 may define the location of a first fold 202a of the closure portion 202.

The first and second pursing strips 209, 210 may be positioned at the same point along the retractable drain 40 such that they are arranged directly opposite each other. They may therefore be laterally squeezed together to form a pair of opposing arcs, opening the drain passage to facilitate flow of the stomal output through the elongate drain passage.

Preferably, each of the pursing strips 209-211 may extend the same distance along a length of the retractable drain 40.

A first fastener 203 may be used to fasten the closure portion 202 in place in its folded state. The first fastener 203 may be arranged on the retractable drain 40, adjacent to or overlapping the closure portion 202.

As shown in FIG. 6, the first fastener 203 may comprise a first flange 203a and a second flange 203b. The second flange 203b may extend from the first flange 203a, the first flange 203a and the second flange 203b may be one integral piece and may meet at a fold line such that the second flange 203b is rotatable about the fold line.

The first flange 203a may be attached to the retractable drain 40 while the second flange 203b hangs free of the retractable drain 40. The first flange 203a may extend across the width of the retractable drain 40 and be attached to the retractable drain 40 at an attachment point, line or zone. The first flange 203a may be attached within an upper region of the closure portion 202. An upper limit of the attachment point, line or zone may coincide with the upper limit 203c of the closure portion 202. The attachment of the first flange 203a may preferably be formed using an adhesive or by welding.

The fold line between the first flange 203a and the second flange 203b may be located coincident with the upper limit 203c. The second flange 203b may be a free flange (i.e. may be unattached to the retractable drain 40 except by its connection to the first flange 203a).

When folded down, the second flange 203b may extend from the upper limit 203c towards the outlet opening 200 such that it extends over the closure portion 202.

The first fastener 203 may include a pull tab 203d for gripping by the user to slide the retractable drain 40 from the retracted configuration to the extended configuration. In the illustrated embodiment, a free end of the second flange 203b may comprise the pull tab 203d.

The second flange 203b may comprise a first fastening element 212a for attachment to a corresponding second fastening element 212b arranged on the closure portion 202. The second fastening element 212b may be attached to the inner drain portion 41 or the first pursing strip 209, such that after the closure portion 202 is folded upwards to close the outlet opening 200, the second fastening element 212b is arranged on an outer face of the retractable drain 40 for fastening to the first fastening element 212a. The first fastening element 212a and the second fastening element 212b may comprise any suitable fastener elements, for example hook-and-loop type fastener elements.

The first fastener 203 may be formed from a flexible sheet material. The flexible sheet material may be more rigid than the flexible sheet material of the inner drain portion 41 and/or the outer drain portion 42.

As described above, the closure portion 202 may comprise a plurality of segments, the segments having approximately equal segment lengths and being separated by fold lines. The length of the second flange 203b may be longer than one segment length but shorter than two segment lengths such that when the closure portion 202 is unfolded, the pull tab 203d does not extend to or beyond the outlet opening 200 of the retractable drain 40 and when the closure portion 202 is folded, the pull tab 203d extends beyond a distal end 214 of the folded retractable drain 40 as shown in FIG. 9b.

The ostomy appliance 1 may further comprise a guide panel 206 and a push element 207 to assist in movement of the retractable drain 40 between its extended and retracted configurations.

As shown in FIG. 2, the guide panel 206 may be arranged on the outer wall 3. The guide panel 206 may comprise flexible sheet material. The material may be the same as the flexible sheet material of the inner wall 2 and/or the outer wall 3.

As shown in FIG. 4, the guide panel 206 may comprise an upper portion 206a which may be arranged on the main body portion 3a of the outer wall 3 and a lower portion 206b which may extend down from the upper portion 206a to overlie an upper region of the retractable drain 40.

The upper portion 206a may have an upper section 206c extending down from an upper edge of the guide panel 206 of uniform width and a lower section 206d which is flared in that its width increases compared to the uniform width of the upper section 206c. The upper section 206c may transition smoothly into the lower section 206d as shown in FIG. 5 such that lateral edges 213a and 213b of the upper portion 206a may each have the form of a straight edge with a smoothly outwardly-curved lower end.

The lower portion 206b may have a lower section 206f extending up from a lower edge of the guide panel 206 of uniform width and an upper section 206e which is flared in that its width increases compared to the uniform width of the lower section 206f. The lower section 206f may transition smoothly into the upper section 206e as shown in FIG. 6 such that lateral edges 213c and 213d of the lower portion 206b may each have the form of a straight edge with a smoothly outwardly-curved upper end.

The lateral edges 213a, 213b of the upper portion 206a may meet the lateral edges 213c, 213d of the lower portion 206b at apexes 213e and 213f.

The upper portion 206a of the guide panel 206 may be attached to the outer face of the outer wall 3 along the lateral edges 213a, 213b of the upper portion 206a. The attachment may be formed by any suitable means, for example by welding or using an adhesive. The upper portion 206a of the guide panel 206 may be positioned to overlie the cavity when viewed from the front (as arranged when the ostomy appliance 1 is being worn).

The lateral edges 213c, 213d of the lower portion 206b are preferably not attached to the retractable drain 40 along all, or a majority of their length.

The upper portion 206a may define a channel 205 between the upper portion 206a of the guide panel 206 and the outer wall 3. The channel 205 may therefore be arranged outside the cavity. The sides of the channel 205 may be demarcated by the attachment of the lateral edges 213a, 213b. A lowermost point of the lateral edges 213a, 213b may define a location of a mouth 205a of the channel 205 as shown in FIG. 5. The mouth 205a may be located at the transition point between the upper portion 206a and the lower portion 206b of the guide panel 206. For example the mouth 205a may be located at the level of the lowermost point of attachment of the upper portion 206a of the guide panel 206 to the outer wall 3. In particular, the mouth 205a may be located at the level of the apexes 213e and 213f as shown in FIG. 5.

The guide panel 206 as a whole may be aligned with the elongate axis 204 of the retractable drain 40 and the upper portion 206a may have a length selected such that the channel 205 has a length sufficient to receive and retain greater than 50% of, optionally greater than 75%, optionally greater than 90%, optionally substantially all of the length of the retractable drain 40 when the retractable drain 40 is in the retracted configuration.

The channel 205 may have a constant width along a majority of its length. This channel width may be marginally wider than the width of the retractable drain 40, such that at least a portion of the retractable drain 40 may in use be slidably received in the channel 205, with limited lateral movement. For example, the channel 205 may be 2 to 5 mm wider than external width of the retractable drain 40, typically 2 to 3 mm wider. The retractable drain 40 may thereby be constrained to move into the channel 205 in a direction substantially parallel with the elongate axis 204.

As shown in FIG. 2, the push element 207 may comprise an elongate strip of sheet material having higher rigidity than the flexible sheet materials of the inner wall 2, the outer wall 3 and/or the guide panel 206. The push element 207 may be a generally planar.

The push element 207 may comprise an upper section 207a and a lower section 207b. The upper section 207a may have a rounded upper edge 207c. The lower section 207b may have a straight lower edge 207d. On assembly of the ostomy appliance 1, the upper section 207a may be slidably received in the channel 205 and the lower section 207b may be fixedly attached to the lower section 40a of the retractable drain 40 and/or the lower portion 206b of the guide panel 206 as explained further below.

The width of the push element 207 may be the same or less than the width of the retractable drain 40 and therefore may have a width narrower than the constant width of the channel 205 such that the push element 207 may be slidably received in the channel 205. The width of the push element 207 may be 85 to 100% of the width of the retractable drain 40. The width of the channel 205 may thereby restrict lateral movement of the push element 207 as it moves into the retracted configuration and ensure that it moves in line with the elongate axis 204.

The lower section 207b of the push element 207 may be attached to the retractable drain 40, in particular to the lower section 40a of the retractable drain 40 and preferably to the outer drain portion 42 of the outer wall 3. Preferably the push element 207 is only attached to the retractable drain 40 at the lower section 207b. The push element 207, for example the lower section 207b thereof, may be attached to the retractable drain 40 at an attachment 207e as shown in FIG. 6. The attachment 207e may be a point, line or zone of attachment. The attachment 207e may use, for example, adhesive or welding. The attachment 207e may extend over a majority or a whole of the lower section 40a of the retractable drain 40.

An upper limit 208a of the attachment 207e may be located at an intermediate point of the retractable drain 40 which may be the intersection between the upper section 40b and the lower section 40a of the retractable drain 40. For example, the upper limit 208a may be located approximately half-way along the length of the retractable drain 40 when the retractable drain 40 is in the extended configuration with the closure portion 202 folded and fastened.

The attachment 207e is preferably in the form of an attachment zone extending across all or substantially all of the width of the push element 207 from the upper limit 208a of the attachment 207e to the lower edge 207d of the lower section 207b of the push element 207. The whole face of the lower section 207b may be attached to the retractable drain 40.

Once assembled and in the extended configuration, the upper section 207a of the push element 207 may extend upwards from the upper limit 208a of the attachment 207e to be slidably received in the channel 205 wherein the rounded upper edge 207c of the push element 207 extends through the mouth 205a of the channel 205 sliding between the outer wall 3 and the guide panel 206.

The upper section 207a is preferably unattached to the retractable drain 40. The upper limit 208a may therefore represent the uppermost position on the retractable drain 40 at which the push element 207 is attached to the retractable drain 40 (when the retractable drain 40 is in the extended configuration). The upper section 207a may have a length configured to be long enough such that at least a part of the upper section 207a is still received in the channel 205 when the retractable drain 40 is in the extended configuration.

The first fastener 203 may be directly attached, for example using adhesive, to the push element 207, preferably to the lower section 207b of the push element 207. As noted above, the push element 207 may be directly attached to the outer drain portion 42 of the outer wall 3. The first fastener 203 may thereby be indirectly attached to the outer wall 3.

The first fastener 203 and the push element 207 may be arranged such that the first fastener 203 is operable to fasten the closure portion 202 in a folded or otherwise turned-up state when the retractable drain 40 is in the extended configuration. The first fastener 203 may be arranged to hang below the upper limit 208a of the attachment 207e of the push element 207 to the retractable drain 40. The fastening of the first fastener 203 may therefore be independent of the position of the upper section 207a of the push element 207 in the channel 205. The first fastener 203 may thereby be configured to be operable independently of the position of the push element 207. The first fastener 203 and the push element 207 may be formed as separate components. In particular, this enables the fastening and unfastening of the first fastener 203 when the retractable drain 40 is in the extended configuration.

The lower portion 206b of the guide panel 206 may be attached to the retractable drain 40 at an intermediate location along the retractable drain 40. Additionally or alternatively, as shown in FIG. 9b, the lower portion 206b of the guide panel 206 may be attached to the lower section 207b of the push element 207 which, as noted above, may itself be attached to the retractable drain 40.

The lower portion 206b, for example a lower end thereof, may be attached to the retractable drain 40 and/or the push element 207 at an attachment 207f as shown in FIG. 9b. The attachment 207f may be a point, line or zone of attachment. The attachment 207f may use, for example, adhesive or welding. Note, the attachments 207e and 207f are shown schematically in FIG. 9b but omitted, for clarity, from FIGS. 9a and 9c.

An upper limit 208b of the attachment 207f may be located at an intermediate point of the retractable drain 40. For example, the upper limit 208b may be located approximately half-way along the length of the retractable drain 40 when the retractable drain 40 is in the extended configuration with the closure portion 202 folded and secured. The attachment 207f may be positioned opposite the location of the attachment 207e.

The lower portion 206b of the guide panel 206 may thereby act as a tether, preventing movement of the push element 207 fully out of the channel 205 on extension of the retractable drain 40. The attachment 207f may preferably extend across the width of the retractable drain 40 and/or the push element 207, thereby assisting in maintaining the alignment of the retractable drain 40 and push element 207 within the channel 205 during retraction of the retractable drain 40.

The lower section 207b of the push element 207 may overlap the closure portion 202 of the retractable drain 40. The overlap may have a length which is the same as or longer than the length of a fold segment of the closure portion 202. As shown in FIG. 6, a longitudinal gap 221 may be provided between the lower edge 207d of the push element 207 and an upper edge of the second pursing strip 210. The longitudinal gap 221 may define the location of a second fold 202b of the closure portion 202.

Therefore, once the closure portion 202 is folded, the segments of the closure portion 202 below the second fold 202b may overlie the lower section 207b of the push element 207, and the lower edge 207d of the push element 207 may be arranged adjacent the distal end 214 of the folded retractable drain 40.

In use, the ostomy appliance 1 may be mounted to the body of the ostomate using the ostomy wafer 7. The ostomy appliance 1 may adopt an unfolded configuration and a folded configuration. Preferably in both the unfolded configuration and the folded configuration the periphery of the ostomy wafer 7 does not extend beyond the periphery of the inner wall 2 and the outer wall 3 such that the ostomy wafer 7 is hidden from view.

Advantageously, the ostomy appliance 1 may be mounted to the ostomate with the lower apex 9b lowermost, e.g. closest to the ground when the ostomate is standing. It has been found that the combination of a cavity formed from an inner wall 2 and an outer wall 3 of rectangular, preferably square, shape which are orientated with one apex 9 lowermost may provide beneficial shaping of the ostomy appliance 1 when filled. In particular, it has been found that the edges 10a-d of the inner wall 2 and outer wall 3 may be subjected to less crinkling when the cavity is filled and also that the opposed lateral apexes 9c, 9d may be able to lie closer to the body of the ostomate when the cavity is filled. This can lead to a reduced degree of pulling on the ostomy wafer 7 and a reduction in the visual bulk of the ostomy appliance 1 beneath clothing.

In addition, it has been found advantageous to position one apex 9 lowermost where the ostomy appliance 1 is intended to be mounted to the torso region of the ostomate. In this way discretion may be enhanced as the ostomy appliance 1 may more easily be perceived by third parties as a loose article of clothing, e.g. a shirt tail, rather than a medical device.

In the folded configuration the cavity may have a first useable volume which may be 120 to 400 ml. In the unfolded configuration the cavity may have a second useable volume which may be 350 to 650 ml.

Typically, a user after first mounting the ostomy appliance 1 will configure the ostomy appliance 1 into its folded state. The ostomy appliance 1 can be brought into the folded state by folding the inner wall 2 and the outer wall 3 as well as the inner comfort layer 5 and the outer comfort layer 6 of one or more of the peripheral regions 11a-d inwardly or outwardly into their folded configuration to overlie the at least one adjacent region 12a-d. This folding involves an 'external' fold (towards or away from the body of the ostomate) of the inner wall 2 and the outer wall 3 (and where present the inner comfort layer 5 and the outer comfort layer 6) such that the inner wall 2 (I) and the outer wall 3 (O) are each rotated about the fold line 16c-d in the same sense, i.e. either both the inner wall 2 and the outer wall 3 being folded towards the body of the ostomate or both the inner wall 2 and the outer wall 3 being folded away from the body of the ostomate. For example, in the case of an external fold towards the body of the ostomate, after the external fold has been completed, the wall layers are ordered OIIO when listed from an outer side of the ostomy appliance to an inner side of the ostomy appliance (where 'O' stands for an outer wall layer and 'I' stands for an inner wall layer). In another example, in the case of an external fold away the body of the ostomate, after the external fold has been completed, the wall layers are ordered IOOI when listed from an outer side of the ostomy appliance to an inner side of the ostomy appliance. This is in contrast to the formation of a pocket where the inner wall 2 and outer wall 3 are pushed 'internally' to form a pocket. In the case of a pocket the wall layers are ordered OOII when listed from an outer side of the ostomy appliance to an inner side of the ostomy appliance.

When in use and in its folded configuration, the at least one peripheral region 11a-d may preferably be located between the adjacent region 12a-d and a body of an ostomate wearing the ostomy appliance 1.

A portion of the at least one peripheral region 11a-d may be inserted into one of the openings, for example slits 21, to releasably retain the at least one peripheral region 11*a-d* in its folded configuration. The one or more openings of the at least one comfort layer 5, 6 may be configured to receive and to releasably retain an apex 9 of the at least one peripheral region 11*a-d*.

In some embodiments both lateral wing regions 11*c*, 11*d* may be folded inwardly. The ostomy appliance 1 may thus be folded into a substantially hexagonal shape in its folded state.

In some embodiments only one lateral wing region 11*c*, 11*d* is folded inwardly. Additionally or alternatively, other peripheral regions 11*a*, 11*b* may be folded inwardly, for example the upper peripheral region 11*a* encompassing the upper apex 9*a* may be folded downwardly. Additional openings in the inner comfort layer 5 may be provided to retain these other peripheral regions, for example horizontally-orientated openings.

Advantageously, the stiffening members 17, 18 may act to rigidify the one or more peripheral regions 11*a-d* to make them easier to fold and to improve retention in the openings, for example slits 21. Further, the stiffening members 17, 18 may advantageously help to define and control the location of fold lines 16*c-d*.

In its folded state the ostomy appliance 1 can receive a quantity of stomal output while retaining the one or more peripheral regions 11*a-d* in their folded configuration. Advantageously, during this period of use the ostomy appliance 1 may be more discreet due to its reduced footprint. In some embodiments the ostomy appliance 1 provides a relatively slim width due to the folded lateral wing regions 11*c*, 11*d* which is more easily hidden under clothing.

As the cavity continues to fill a point will be reached where the one or more peripheral regions 11*a-d* will be unfolded so that the ostomy appliance 1 is brought into its unfolded configuration. The at least one peripheral region 11*a-d* may be spontaneously unfoldable from its folded configuration when the cavity is subject to a build-up of pressure. The build-up of pressure may be due to an increase in gas pressure and/or fluid pressure. Advantageously, the unfolding may take place without manual intervention by the ostomate, i.e. solely under the driving force of the build-up of internal pressure in the cavity which overcomes the retaining force imparted by the inner comfort layer 5 on the at least one peripheral region 11*a-d*.

Thus, as the cavity fills the at least one peripheral region 11*a-d* can 'spring' or 'slide' or 'pop' free of the opening in the inner comfort layer 5 allowing the at least one peripheral region 11*a-d* to unfold and increase the useable volume of the cavity.

Advantageously, the user may also choose to manually unfold the at least one peripheral region 11*a-d* which promotes user-control of their ostomy appliance 1.

During use, the user can inspect the cavity by pulling apart the first part 6*a* and the second part 6*b* of the outer comfort layer 6 to open a window opening 33. The oblique angling of the window opening 33 may beneficially maximise the size of the window opening 33 and may also provide a more ergonomic orientation of the window opening 33 when the ostomy appliance 1 is mounted to the torso of an ostomate.

In use, inside the cavity stomal output is received in the first chamber 101 from the stomal inlet 20. Stomal liquid and stomal gas are filtered through the separation filter 100 to the second chamber 102 whilst the stomal solids remain in the first chamber 101. The stomal liquid substantially remains within the second chamber 102 (although residual amounts will also remain in the first chamber 101) and the stomal gas is able to exit the ostomy appliance 1 via the gas vent 27. The stomal solids are substantially prevented from reaching the gas vent 27 by the separation filter 100. The protective structure 110 receives the gas through the protective chamber gas inlet 112 and communicates the gas through the protective chamber 111 to the gas vent 27.

The functioning of the retractable drain 40 will now be described starting with the retractable drain 40 in the extended configuration as shown in FIGS. 1 to 6.

Figure 7A:
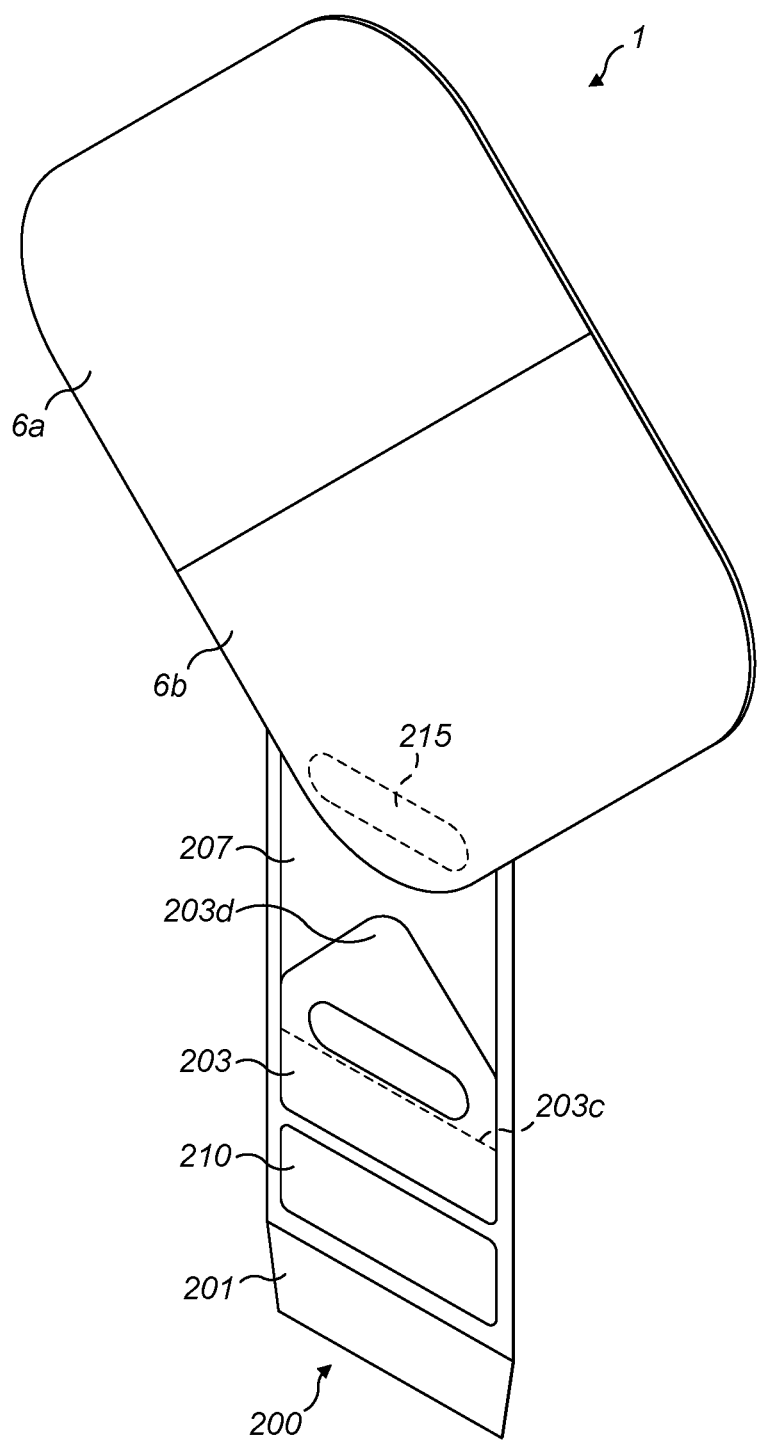
FIGS. 7a to 7d schematically illustrate the retractable drain of the ostomy appliance of FIG. 1 in a) the extended configuration b) the extended configuration with the closure portion folded c) the extended configuration with the closure portion folded and fastened and d) the retracted configuration.

In the extended configuration, as shown in FIGS. 7*a* and 9*a*, the retractable drain 40 may extend through the opening 130 and the retractable drain 40 and its closure portion 202 may be entirely unfolded such that stomal output may move from the cavity down the elongate drain passage of the retractable drain 40 and out of the outlet opening 200.

Passage of the stomal output out of the outlet opening may be facilitated by pressing on the pursing strips 209-211 to hold open the outlet opening 200 and/or to curve the lip 201 into a chute shape to guide the exiting flow of stomal output.

Figure 7B:
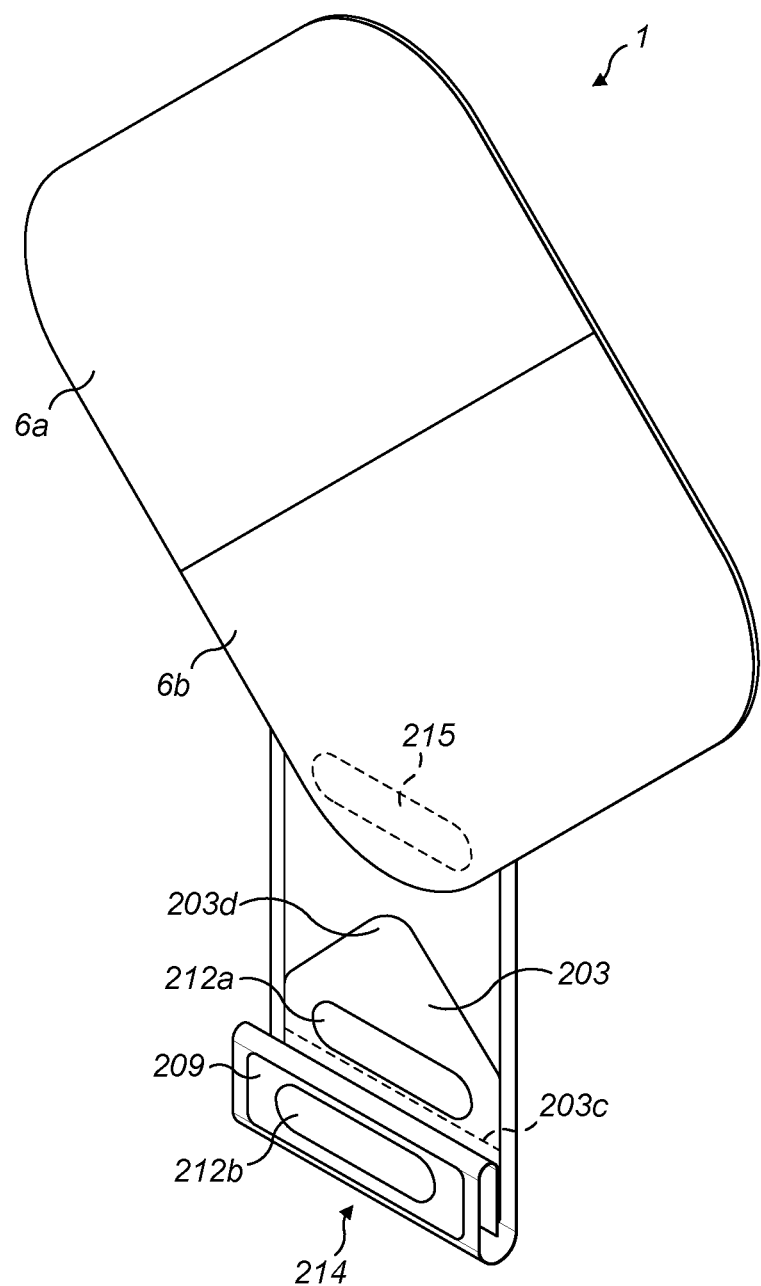
Figure 7C:
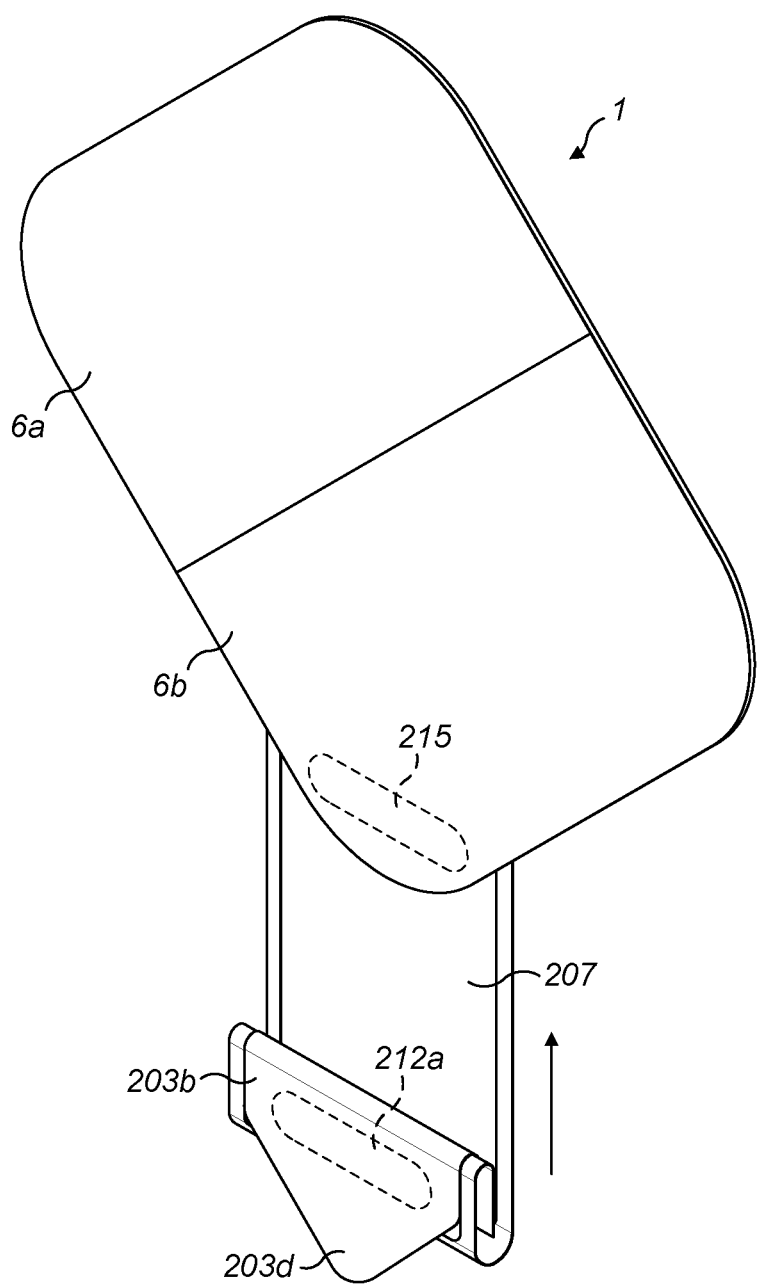
Figure 7D:
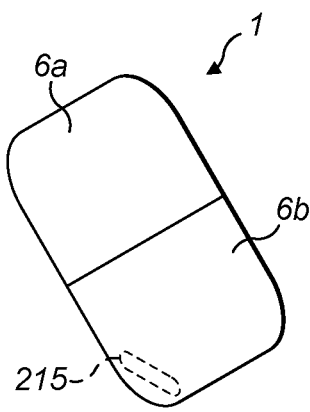

After emptying the cavity, the outlet opening 200 may be sealed to prevent flow of stomal output out of the retractable drain 40. As shown in FIGS. 7 to 9, with the retractable drain 40 in the extended configuration, the outlet opening 200 may first be sealed by operation of the closure portion 202 which may be folded over at least once, and preferably a plurality of times. For example, the lip 201 may first be folded upwards about the first fold 202*a* to overlie the first pursing strip 209. Next the lip 201 and the next segment bearing the first pursing strip 209 and second pursing strip 210 may be folded upwards, about the second fold 202*b* to overlie the first flange 203*a* and lower section 207*b* of the push element 207 as shown in FIG. 7*b*. The second flange 203*b* of the first fastener 203 may then be folded over to fasten the closure portion 202 in its folded position by securing together the first and second fastening element 212*a*, 212*b* as shown in FIG. 7*c*. The user may then, if desired, let go of the retractable drain 40 if needed without stomal output being released through the outlet opening 200.

To move the retractable drain 40 into the retracted configuration after folding and fastening of the closure portion 202, the user may grip the folded and fastened end of the retractable drain 40 and push upwards such that the push element 207 moves further up into the channel 205 as shown in FIG. 9*b*.

Movement of the push element 207 may be used to create one more folds in the retractable drain 40 so as to shorten its length in the retracted configuration and to close off the elongate drain passage.

Due to the attachment 207*e* between the push element 207 and the outer drain portion 42, the resulting upward movement of the push element 207 causes the lower section 40*a* of the retractable drain 40 to be carried up and the unattached upper section 40*b* of the retractable drain 40 to start to bend away from the push element 207 as shown in FIG. 9*b* resulting in the formation of a first fold 216 and a second fold 217 in the retractable drain 40.

As the push element 207 moves up the second fold 217 will start to form at the location of the upper limit 208*a* since the upper section 40*b* is unattached to the push element 207 and is thus free to move away therefrom. The associated first fold 216 forms intermediate the upper end of the retractable drain 40 and the second fold 217 as shown in FIG. 9*b*.

At the same time upward movement of the push element 207 may likewise cause the formation of a first fold 218 and a second fold 219 in the lower portion 206*b* of the guide panel 206 as shown in FIG. 9*b*. The second fold 219 will start to form at the location of the upper limit 208*b* since lower portion 206b above the upper limit 208b is unattached to the push element 207 and is thus free to move away therefrom. The associated first fold 218 forms intermediate the upper end of the lower portion 206b and the second fold 219 as shown in FIGS. 9b and 9c.

Continued upward movement of the push element 207 may thus cause the retractable drain 40 to double back on itself and the lower portion 206b of the guide panel 206 to double back on itself.

In the fully retracted configuration as shown in FIG. 9c, the retractable drain 40 may comprise a generally Z-shaped form by virtue of the fully formed first fold 216 and second fold 217.

The first fold 216 and the second fold 217 preferably extend fully across the retractable drain 40 such that the first and second folds 216, 217 close off the elongate drain passage and inhibit drainage of stomal output through the retractable drain 40. As can be seen in FIG. 9c, the lower end of the separation wall 4 extends below the final location of the first fold 216 such that the second fold 216 may effectively seal of the lower end of the first and second chambers 101, 102 when the retractable drain 40 is in its retracted configuration.

The first and second folds 216, 217 may be folded in opposite senses such that the upper section 40b of the retractable drain 40 overlies the cavity adjacent to the main body portion 3a of the outer wall 3 and the lower section 40a of the retractable drain 40 overlies the upper section 40b, such that all of the retractable drain 40 directly or indirectly overlies the main body portion 3a of the outer wall 3.

In the retracted configuration, the first fold 216 may have rolled up the upper section 40b of the retractable drain 40 to be located at or adjacent the drain inlet 45. The second fold 217 may be located approximately halfway along the length of the retractable drain 40 such that in the retracted configuration the distal end 214 of the retractable drain 40 (with the closure portion 202 folded) is arranged adjacent to the first fold 216 as shown in FIG. 9c.

The channel 205 may have a depth between the guide panel 206 and the outer wall 3 configured such that the retractable drain 40 is a tight sliding fit in the channel 205 in the depth direction when the retractable drain 40 is in the retracted configuration.

The folds 216, 217 formed in the retractable drain 40 as it moves into the retracted configuration may thereby be formed generally perpendicular to the length of the retractable drain 40. This may also assist in ensuring that greater than 50% of, optionally greater than 75%, optionally greater than 90%, optionally substantially all of the length of the retractable drain 40 (with the closure portion 202 folded) may be received within the channel 205 in the retracted configuration.

The channel 205 of the upper portion 206a of the guide panel 206 may have a length which is at least half the length of the retractable drain 40 when the retractable drain 40 is in the extended configuration with the closure portion 202 folded. Preferably, the channel 205 may have a length marginally longer than the length of the push element 207 such that a majority of or substantially all of the push element 207 may be received in the channel 205 in the retracted configuration.

Once the retractable drain 40 is in its retracted configuration the fastening element 215a, 215b may be secured together as shown in FIG. 9c.

As the outlet opening 200 of the retractable drain 40 may be sealed before retraction, and may then substantially wholly be received through the opening 130 between the inner comfort layer 5 and the outer comfort layer 6, the outlet opening 200 of the retractable drain 40 may remain sealed while in the retracted configuration.

Further example embodiments of an ostomy appliance 1 according to the present disclosure are described below. Only those features that differ in this embodiment compared to the previous embodiment will be described in detail in the following description. For features that are common to one or more embodiments, reference should be made to the description as a whole.

Figure 10A:
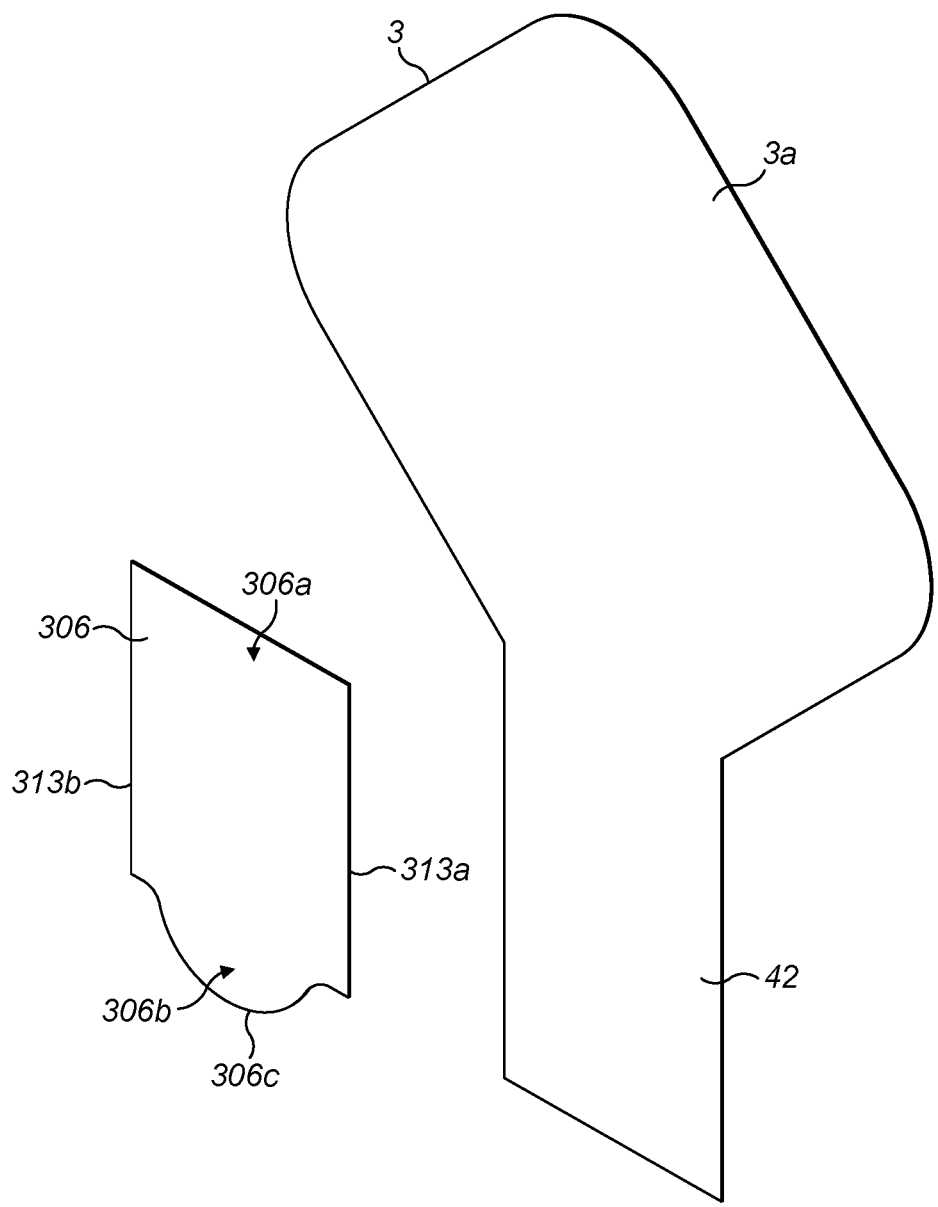
FIGS. 10a and 10b illustrate a schematic views of a further embodiment of ostomy appliance according to the present disclosure with the retractable drain in the extended configuration.
Figure 10B:
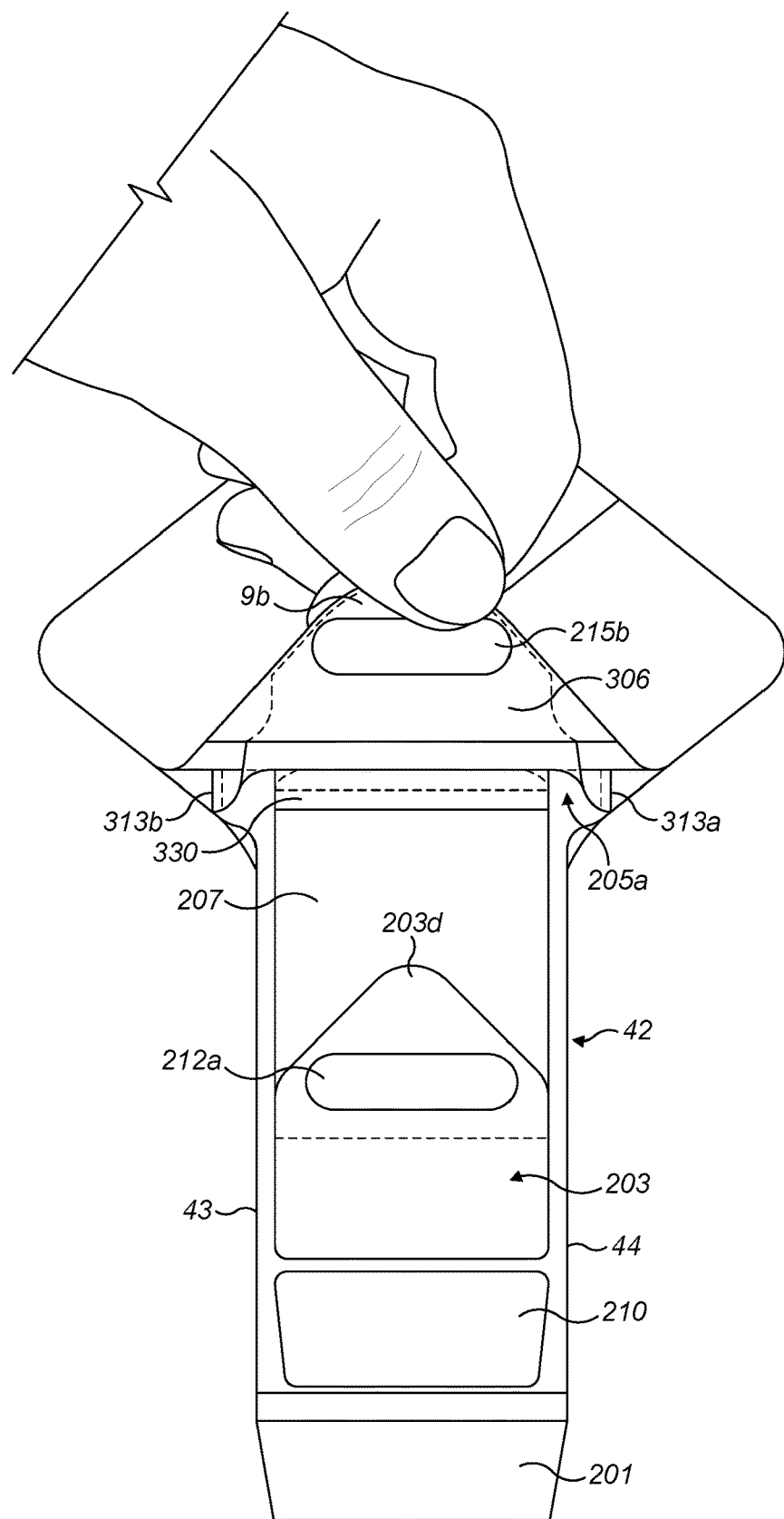

In any embodiment, the lower portion 206b of the guide panel 206 may take a different form to that shown in FIGS. 1 to 9. An alternative form of guide panel is shown in FIGS. 10a and 10b. The guide panel 306 may comprise an upper portion 306a defining the channel 205 as in the embodiment of FIGS. 1 to 9 demarcated between lateral edges 313a and 313b of the upper portion 306a. The mouth 205a of the channel 205 may be located at the transition point between the upper portion 306a and the lower portion 306b of the guide panel 306.

The lower portion 306b of the may have a lower edge 306c shaped such that it does not extend outside the outer comfort layer 6 in use. The lower portion 306b may therefore have a truncated shape compared to the lower portion 206b of guide panel 206. The lower edge 306c may be shaped to match the curve of the lower apex of the outer comfort layer 6. The lower portion 9b may be attached to the lower apex of the outer comfort layer 6, for example by use of adhesive or by welding, at or adjacent to the opening 130 of the comfort layer. Opening of the closure 215 to open opening 130 may tend to open out the mouth 205a of the channel 205, facilitating extension and retraction of the retractable drain 40 in use.

The lower portion 306a may be unattached to the drain 40. A separate tether may be provided for tethering the push element 207 in the channel 205. The separate tether may be attached to the drain by an attachment 330 formed, for example, by use of adhesive or by welding.

In any embodiment, the outlet opening 200 of the retractable drain 40 may be configured for connection of a night bag or other appliance for receiving stomal output from the retractable drain 40.

Other features of the ostomy appliance, for example the shape and construction of the ostomy appliance inner and outer walls and comfort layer, may vary from those shown in the illustrated embodiment.

In any embodiment, the retractable drain may alternatively be formed as a one-piece tube rather than from two sheets joined by lateral welds. The retractable drain may be integrally formed with the inner wall and/or the outer wall of the appliance. Alternatively, or in addition, one or more parts of the retractable drain may be formed from flexible sheet material or other material separately to the formation of the inner wall and/or the outer wall, and assembled by any suitable means, for example by welding or using adhesives.

The fastening elements illustrated are hook-and-loop type elements. Alternatively, any form of suitable fastener elements may be used (for example, poppers, zippers or adhesives).

The channel may be formed on the inner wall rather than outer wall of the cavity.

The guide panel is preferably formed separately to the comfort layer. Alternatively, the guide panel may comprise a portion of the comfort layer. Alternatively, or in addition, the guide panel may be arranged on the inner wall or the outer wall and attached to the comfort layer instead of or as well as being attached to the wall.

In addition or alternatively to the closure 215 and first fastener 203, alternative means of sealing the outlet opening 200 in the extended configuration may be provided. In any embodiment, the upper limit 208a of the attachment of the push element 207 to the retractable drain 40 may be arranged approximately halfway along the length of the retractable drain 40 with the outlet opening 200 of the drain sealed in the extended configuration.

One or both comfort layers 5, 6 may optionally be omitted or formed from alternative materials to display the outer wall 3 and/or inner wall 2, for example for hospital use.

In the illustrated embodiment, the closure portion 202 is configured to be turned up by folding. Alternatively, or additionally, in any embodiment the closure portion 202 may be turned up by rolling.

Examples

The following table presents example configurations of an ostomy appliance 1 according to the present disclosure. These examples are not intended to be limiting on the present disclosure in any way or to limit the scope of the appended claims. Rather, the examples are provided to aid a better understanding of the present disclosure.

The examples refer to features described in further detail elsewhere in the present disclosure. The skilled reader will understand that reference should be made to said further description where necessary for a fuller understanding of the examples. Where said further description refers to optional characteristics of said features then the skilled reader will understand that the following examples may optionally also include one or more of said optional characteristics.

General Construction

In the following examples in the table, the ostomy appliance 1 is a one-piece ostomy appliance 1 wherein the ostomy wafer 7 is permanently attached to the ostomy appliance 1, to the extent that the ostomy wafer 7 cannot easily be separated without risk of damaging the ostomy appliance 1. However, as noted above the teachings of this disclosure may also be applied, with suitable alteration where necessary, to two-piece appliances. The ostomy appliance 1 of the following examples is particularly suited as an ileostomy appliance but is not limited to this function.

In the following examples in the table, the ostomy appliance 1 comprises an inner wall 2 and an outer wall 3 which are diamond-shaped having four apexes—an upper apex 9a which points generally vertically upwards, a lower apex 9b which points generally vertically downwards and opposed lateral apexes 9c, 9d which point generally to each side. A retractable drain 40 is present and extends from the lower apex 9b. The apexes 9a-9d are rounded with a radius of curvature of about 30 mm.

In the following examples in the table, the inner wall 2 and the outer wall 3 comprise a left lateral wing region 11d terminating in lateral apex 9d and a right lateral wing region 11c terminating in lateral apex 9c. As described above, the lateral wing regions 11c, 11d are foldable about fold lines 16c, 16d to overlie adjacent regions 12c, 12d in a folded configuration of the ostomy appliance 1.

In this table, the term "Wall Size" refers to the length of the sides of the inner wall 2 and the outer wall 3. The 'length' is measured as the perpendicular distance between opposite sides of the inner wall 2/outer wall 3. In the following examples in the table the length of each side is the same, i.e. the inner wall 2 and the outer wall 3 are generally square-shaped but with rounded corners as noted above.

In this table, the term "Separation Filter" refers to whether a separation wall 100 as described above is present. The separation wall 100, where present, is located between the inner wall 2 and the outer wall 3. The separation wall 4 comprises a separation filter 100 for filtering stomal gases and/or stomal liquids from stomal solids contained in the stomal output.

The inner wall 2 and outer wall 3 are formed from EVA/PVdC multi-layered film of 75 micrometres thickness. The separation wall 100 (where present) is formed from PE film of 51 micrometres thickness or EVA (with 4.5% VA) film of 50 micrometres thickness.

The following examples may comprise at least an inner comfort layer 5 as described above that comprises two vertical slits 21 as described above for receiving the lateral apexes 9c, 9d of the inner wall 2 and the outer wall 3 when the ostomy appliance 1 is in its folded configuration.

In the following examples the ostomy appliance is an open appliance that comprises a retractable drain 40. The retractable drain may be a retractable drain 40 as described above.

In this table, the term "Wafer Size" refers to the length of the sides of the ostomy wafer 7. The 'length' is measured as the perpendicular distance between opposite sides of the ostomy wafer. In the following examples in the table the length of each side is the same, i.e. the ostomy wafer 7 is square-shaped but with rounded corners as shown in the appended figures.

In this table, the term "Wafer Type" refers to the configuration of the ostomy wafer 7: "Flat" refers to an ostomy wafer 7 that is flat in shape. "Convex" refers to an ostomy wafer 7 that is convex in shape. "Flexible" refers to an ostomy wafer 7 that is flexible.

In this table, the term "Wafer Aperture Type" refers to the nature of the aperture in the ostomy wafer 7: "Pre-Cut" refers to the presence of a pre-formed aperture in the ostomy wafer 7 for engaging in, on, over or against the stoma of an ostomate. "Cut-To-Fit" refers to an ostomy wafer 7 configured to allow an ostomate to cut an aperture therein for engaging in, on, over or against their stoma. In this way the aperture may be tailored to the specific requirements of each ostomate.

In this table, the term "Aperture Size" refers to the diameter of the pre-formed aperture in the ostomy wafer 7 in the case of a Pre-Cut ostomy wafer and refers to the range of possible aperture diameters that may be formed in the ostomy wafer 7 in the case of a Cut-To-Fit ostomy wafer.

In this table, the column "Colour" refers to the colour of the outermost layer of the ostomy appliance. "Neutral" refers to the presence of an outer comfort layer 6 having an opaque, neutral colour. In these examples the outer wall 3 is transparent and the inner wall 2 is opaque, e.g. white. "Clear" refers to an ostomy appliance without an outer comfort layer 6. In these examples the outermost layer is the outer wall 3 which is transparent. The inner wall 2 is opaque, e.g. white. All examples are provided with an inner comfort layer 5 that is an opaque, neutral colour. By "transparent" is meant a material that is substantially or fully transparent, or sufficiently translucent to permit viewing of the fill-level of the cavity through the outer wall 3.

TABLE

| Example No. | Wafer Type | Wafer Size (mm) | Wafer Aperture Type | Aperture Size (mm) | Wall Size (mm) | Colour | Separation Filter? |
|---|---|---|---|---|---|---|---|
| 1 | Flat | 98 | Cut-To-Fit | 10-50 | 140 | Neutral | Yes |
| 2 | Flat | 98 | Pre-Cut | 25 | 140 | Neutral | Yes |
| 3 | Flat | 98 | Pre-Cut | 30 | 140 | Neutral | Yes |
| 4 | Flat | 98 | Pre-Cut | 35 | 140 | Neutral | Yes |
| 5 | Flat | 107 | Cut-To-Fit | 10-60 | 170 | Neutral | Yes |
| 6 | Flat | 107 | Pre-Cut | 25 | 170 | Neutral | Yes |
| 7 | Flat | 107 | Pre-Cut | 30 | 170 | Neutral | Yes |
| 8 | Flat | 107 | Pre-Cut | 35 | 170 | Neutral | Yes |
| 9 | Flat | 107 | Pre-Cut | 40 | 170 | Neutral | Yes |
| 10 | Flat | 107 | Cut-To-Fit | 10-60 | 170 | Clear | Yes |
| 11 | Flat | 107 | Cut-To-Fit | 10-60 | 170 | Clear | No |
| 12 | Flat | 107 | Pre-Cut | 25 | 170 | Clear | Yes |
| 13 | Flat | 107 | Pre-Cut | 30 | 170 | Clear | Yes |
| 14 | Flat | 107 | Pre-Cut | 35 | 170 | Clear | Yes |
| 15 | Flat | 107 | Pre-Cut | 40 | 170 | Clear | Yes |
| 16 | Convex | 107 | Cut-To-Fit | 10-55 | 170 | Clear | Yes |
| 17 | Convex | 107 | Cut-To-Fit | 10-55 | 170 | Neutral | Yes |
| 18 | Convex | 98 | Cut-To-Fit | 10-45 | 140 | Neutral | Yes |
| 19 | Convex | 107 | Cut-To-Fit | 10-45 | 170 | Neutral | Yes |
| 20 | Convex | 107 | Cut-To-Fit | 10-45 | 170 | Clear | Yes |
| 21 | Convex | 107 | Pre-Cut | 25 | 170 | Neutral | Yes |
| 22 | Convex | 107 | Pre-Cut | 30 | 170 | Neutral | Yes |
| 23 | Convex | 107 | Pre-Cut | 35 | 170 | Neutral | Yes |
| 24 | Convex | 98 | Cut-To-Fit | 10-35 | 140 | Neutral | Yes |
| 25 | Convex | 107 | Cut-To-Fit | 10-35 | 170 | Neutral | Yes |
| 26 | Convex | 107 | Pre-Cut | 25 | 170 | Neutral | Yes |
| 27 | Convex | 107 | Pre-Cut | 30 | 170 | Neutral | Yes |
| 28 | Convex | 107 | Pre-Cut | 35 | 170 | Neutral | Yes |
| 29 | Convex | 98 | Cut-To-Fit | 10-25 | 140 | Neutral | Yes |
| 30 | Convex | 107 | Cut-To-Fit | 10-25 | 170 | Neutral | Yes |
| 31 | Flexible | 107 | Cut-To-Fit | 10-55 | 170 | Clear | Yes |
| 32 | Flexible | 107 | Cut-To-Fit | 10-55 | 170 | Neutral | Yes |
| 33 | Flexible | 98 | Cut-To-Fit | 10-45 | 140 | Neutral | Yes |
| 34 | Flexible | 107 | Cut-To-Fit | 10-45 | 170 | Neutral | Yes |
| 35 | Flexible | 107 | Cut-To-Fit | 10-45 | 170 | Clear | Yes |
| 36 | Flexible | 107 | Pre-Cut | 25 | 170 | Neutral | Yes |
| 37 | Flexible | 107 | Pre-Cut | 30 | 170 | Neutral | Yes |
| 38 | Flexible | 107 | Pre-Cut | 35 | 170 | Neutral | Yes |
| 39 | Flexible | 98 | Cut-To-Fit | 10-35 | 140 | Neutral | Yes |
| 40 | Flexible | 107 | Cut-To-Fit | 10-35 | 170 | Neutral | Yes |
| 41 | Flexible | 107 | Pre-Cut | 25 | 170 | Neutral | Yes |
| 42 | Flexible | 107 | Pre-Cut | 30 | 170 | Neutral | Yes |
| 43 | Flexible | 107 | Pre-Cut | 35 | 170 | Neutral | Yes |
| 44 | Flexible | 98 | Cut-To-Fit | 10-25 | 140 | Neutral | Yes |
| 45 | Flexible | 107 | Cut-To-Fit | 10-25 | 170 | Neutral | Yes |

It is to be understood that at least some of the figures and descriptions of the disclosure have been simplified to focus on elements that are relevant for a clear understanding of the disclosure, while eliminating, for purposes of clarity, other elements that the reader skilled in the art will appreciate may also be required. Because such elements are well known to the reader skilled in the art, and because they do not necessarily facilitate a better understanding of the disclosure, a description of such elements is not provided herein.

The invention claimed is:

1. An ostomy appliance comprising:
 inner and outer walls of flexible sheet material joined together to define a cavity for containing a stomal output, the inner wall comprising an inlet for receiving the stomal output into the cavity;
 a retractable drain being slidably movable between an extended configuration for draining the stomal output from the cavity and a retracted configuration for storage of the retractable drain; and
 a push element for pushing the retractable drain into the retracted configuration, the push element comprising a strip of material having higher rigidity than the flexible sheet material of the inner wall and/or the outer wall;
 wherein the retractable drain comprises a closure portion which may be turned up to close an outlet opening of the retractable drain and a first fastener configured to fasten the closure portion in place once turned up;
 wherein at least a portion of the closure portion and the first fastener are positioned in a channel when the retractable drain is in the retracted configuration;
 wherein the first fastener is configured to be operable independently of the push element, and wherein the push element and the first fastener are formed as separate components.

2. The ostomy appliance according to claim 1 wherein the closure portion is operable to be turned up and fastened while the retractable drain is in the extended configuration.

3. The ostomy appliance according to claim 2 wherein the retractable drain is configured such that after fastening of the closure portion in the extended configuration, the retractable drain is slidably moveable into the retracted configuration.

4. The ostomy appliance as claimed in claim 1 wherein the closure portion is configured to be turned up by forming at least one fold across the retractable drain to inhibit passage of stomal output through the outlet end, wherein the closure portion is configured to be folded into a plurality of folds across the retractable drain to inhibit passage of stomal output through the outlet opening.

5. The ostomy appliance as claimed in claim 1 wherein at least a part of the first fastener is arranged on an intermediate portion of the retractable drain such that the first fastener is adjacent to or overlapping the closure portion;
   wherein the first fastener comprises:
      a first flange attached to the intermediate portion of the retractable drain adjacent to the closure portion; and
      a second flange comprising a first fastening element for attachment to the closure portion;
   wherein the closure portion further comprises a second fastening element for attachment to the first fastening element;
   wherein the first fastener is arranged across the width of the retractable drain;
   wherein the second flange is configured to extend over the closure portion when fastened.

6. The ostomy appliance as claimed in claim 1 wherein the retractable drain further comprises a first pursing strip and a second pursing strip arranged on the closure portion of the retractable drain;
   wherein one or more of the pursing strips comprises a strip of flexible material having higher rigidity than the material forming the retractable drain, the strip being arranged across a width of the retractable drain;
   wherein the first pursing strip is arranged on an outer side of the retractable drain, and the second pursing strip arranged on an inner side of the retractable drain, the first pursing strip and the second pursing strip being positioned at the same distance along the retractable drain such that they are arranged opposite each other;
   the appliance further comprising a lip pursing strip arranged adjacent to the outlet opening of the retractable drain;
   wherein the first pursing strip and the second pursing strip are arranged adjacent to each other and spaced apart to define a folding point of the retractable drain between the first pursing strip and the second pursing strip such that the retractable drain is foldable in increments defined by a length of the first pursing strip and the second pursing strip;
   wherein each of the first pursing strip and second pursing strip extends the same distance along a length of the retractable drain.

7. The ostomy appliance as claimed in claim 1 wherein the retractable drain comprises:
   an inner drain portion extending from a main body portion of the inner wall; and
   an outer drain portion extending from a main body portion of the outer wall;
   wherein the inner and outer drain portions are sealed at their lateral edges to define a drain passage between the inner and outer drain portions;
   wherein the inner drain portion is integrally formed with the main body portion of the inner wall and/or the outer drain portion is integrally formed with the main body portion of the outer wall;
   wherein one of the inner drain portion and the outer drain portion is longer than the other of the inner drain portion and the outer drain portion, thereby defining a lip at the outlet opening of the retractable drain;
   wherein a pursing strip is arranged on the lip.

8. The ostomy appliance as claimed in claim 1 wherein in the retracted configuration drainage of the stomal output from the cavity into the retractable drain and along the retractable drain is inhibited by folds formed across the retractable drain during the sliding retraction; and/or
   wherein in the retracted configuration substantially all of the retractable drain overlies a main body portion of the outer and/or inner wall.

9. The ostomy appliance according to claim 1 wherein the closure portion comprises a folding portion which is foldable to close an outlet opening of the drain.

10. The ostomy appliance according to claim 1 wherein the first fastener comprises a pull tab for gripping by the user to slide the retractable drain from the retracted configuration to the extended configuration.

11. An ostomy appliance comprising:
   inner and outer walls of flexible sheet material joined together to define a cavity for containing a stomal output, the inner wall comprising an inlet for receiving the stomal output into the cavity;
   a retractable drain being slidably movable between an extended configuration for draining the stomal output from the cavity and a retracted configuration for storage of the drain, the retractable drain comprising a closure portion and a first fastener configured to fasten the closure portion in a turned up orientation;
   an inner comfort layer arranged over at least a part of the inner wall;
   an outer comfort layer arranged over at least a part of the outer wall; and
   a push element for pushing the retractable drain into the retracted configuration, the push element comprising a strip of material having higher rigidity than the flexible sheet material of the inner wall and/or the outer wall;
   wherein in the retracted configuration the retractable drain and at least a portion of the closure portion and the first fastener are received in a channel arranged between either the inner wall and the inner comfort layer or the outer wall and the outer comfort layer, the dimensions of the channel being configured such that the retractable drain is slidably held in the channel when in the retracted configuration;
   wherein the inner comfort layer and/or the outer comfort layer defines an opening through which the retractable drain is slidably moveable between the extended and retracted configurations;
   wherein a closure for closing the opening is arranged at or proximal to a lower end of the channel such that the closure restricts sliding of the retractable drain from the retracted configuration;
   wherein the first fastener is configured to be operable independently of the push element, and wherein the push element and the first fastener are formed as separate components.

12. The ostomy appliance as claimed in claim 11 wherein the closure comprises a first closure element arranged on the inner comfort layer and a second closure element arranged on the outer comfort layer.

13. The ostomy appliance as claimed in claim 11 further comprising a guide panel arranged on an outer face of the inner wall or an outer face of the outer wall;
   wherein the channel is defined between the guide panel and the inner wall or the outer wall;
   wherein a lower portion of the guide panel is arranged adjacent to the opening of the channel, the lower portion of the guide panel being attached to the comfort layer;
   wherein the lower portion of the guide panel is attached to the closure such that opening of the closure widens a lower portion of the channel.

14. The ostomy appliance as claimed in claim 11, further comprising a push element for driving the retractable drain into the channel to move the retractable drain into the retracted configuration; and a guide panel arranged out an outer face of a main body portion of the inner wall or a main body portion of an outer face of the outer wall;

wherein the channel is defined between the guide panel and the inner wall or the outer wall;

wherein a lower portion of the guide panel extends downwards from the channel, the lower portion of the guide panel being attached to an intermediate portion of the push element, and wherein the lower portion of the guide panel is attached to the push element across a majority of the width of the retractable drain.

\* \* \* \* \*